United States Patent
Shikhman et al.

(10) Patent No.: US 11,413,050 B2
(45) Date of Patent: Aug. 16, 2022

(54) SURGICAL CLIP AND DEPLOYMENT SYSTEM

(71) Applicant: Oleg Shikhman, Trumbull, CT (US)

(72) Inventors: Oleg Shikhman, Trumbull, CT (US);
Jeffrey Radziunas, Wallingford, CT (US); Brian Michael Lamothe, Hamden, CT (US); Carollynn Goldenberg, Farmington, CT (US)

(73) Assignee: Theragi, LLC, Trumbull, CT (US)

( * ) Notice: Subject to any disclaimer, the term of this patent is extended or adjusted under 35 U.S.C. 154(b) by 140 days.

(21) Appl. No.: 16/772,454

(22) PCT Filed: Dec. 23, 2018

(86) PCT No.: PCT/US2018/067432
§ 371 (c)(1),
(2) Date: Jun. 12, 2020

(87) PCT Pub. No.: WO2019/135958
PCT Pub. Date: Jul. 11, 2019

(65) Prior Publication Data
US 2020/0397445 A1      Dec. 24, 2020

Related U.S. Application Data

(60) Provisional application No. 62/648,593, filed on Mar. 27, 2018, provisional application No. 62/648,586, (Continued)

(51) Int. Cl.
*A61B 17/122*          (2006.01)
*A61B 17/128*          (2006.01)

(52) U.S. Cl.
CPC ...... *A61B 17/1227* (2013.01); *A61B 17/1285* (2013.01)

(58) Field of Classification Search
CPC ... A61B 17/10; A61B 17/122; A61B 17/1227; A61B 17/128; A61B 17/1285
See application file for complete search history.

(56) References Cited

U.S. PATENT DOCUMENTS 4,796,627 A    1/1989  Tucker
4,832,027 A    5/1989  Utz
(Continued)

FOREIGN PATENT DOCUMENTS

KR      101765648        8/2017
WO    WO 2001/035832     5/2001
WO    WO 2019/135958     7/2019

OTHER PUBLICATIONS

European Search Report 18898852.1 Dated 08.19.2021.
(Continued)

*Primary Examiner* — Ryan J. Severson
(74) *Attorney, Agent, or Firm* — Neil D. Gershon

(57) ABSTRACT

A system for compressing body tissue including a clip having first and second tissue contacting surfaces. The clip is movable from a closed position to an open position wherein the clip receives tissue between the first and second tissue contacting surfaces to compress tissue between the first and second tissue contacting surfaces. A clip deployment device has a first clip engagement member and a second clip engagement member engageable with the clip, the first and second clip engagement members movable between first and second positions to controllably move the clip from the closed position to the open position.

20 Claims, 25 Drawing Sheets

Related U.S. Application Data filed on Mar. 27, 2018, provisional application No. 62/613,902, filed on Jan. 5, 2018.

(56) References Cited

U.S. PATENT DOCUMENTS

| | | | |
|---|---|---|---|
| 5,259,366 A | 11/1993 | Reydel et al. | |
| 5,779,720 A | 7/1998 | Walder-Utz et al. | |
| 6,428,548 B1 | 8/2002 | Durgin et al. | |
| 6,849,078 B2 | 2/2005 | Durgin et al. | |
| 6,911,032 B2 | 6/2005 | Jugenheimer et al. | |
| 7,488,334 B2 | 2/2009 | Jugenheimer et al. | |
| 7,806,904 B2 | 10/2010 | Carley et al. | |
| 7,815,565 B2 | 10/2010 | Stefanchik et al. | |
| 7,892,244 B2* | 2/2011 | Monassevitch | A61B 17/0643 606/151 |
| 8,043,307 B2 | 10/2011 | Jugenheimer et al. | |
| 8,187,286 B2 | 5/2012 | Jugenheimer et al. | |
| 8,192,349 B2 | 6/2012 | Schurr et al. | |
| 8,469,995 B2 | 6/2013 | Cummins et al. | |
| 8,518,057 B2 | 8/2013 | Walberg et al. | |
| 8,685,043 B2 | 4/2014 | Jugenheimer et al. | |
| 8,685,048 B2 | 4/2014 | Adams et al. | |
| 8,709,027 B2 | 4/2014 | Adams et al. | |
| 8,721,528 B2 | 5/2014 | Ho et al. | |
| 8,784,436 B2 | 7/2014 | Ho et al. | |
| 8,888,792 B2 | 11/2014 | Harris et al. | |
| 8,974,371 B2 | 3/2015 | Durgin et al. | |
| 9,017,349 B2 | 4/2015 | Privitera et al. | |
| 9,055,942 B2* | 6/2015 | Balbierz | A61F 5/0036 |
| 9,138,227 B2 | 9/2015 | Schostek et al. | |
| 9,149,276 B2 | 10/2015 | Voss | |
| 9,215,968 B2 | 12/2015 | Schostek et al. | |
| 9,295,470 B2 | 3/2016 | Baur et al. | |
| 9,370,369 B2 | 6/2016 | Size et al. | |
| 9,522,040 B2 | 12/2016 | Anhoeck et al. | |
| 9,603,614 B2 | 3/2017 | Schurr et al. | |
| 9,957,356 B2 | 5/2018 | Zhang et al. | |
| 10,166,024 B2* | 1/2019 | Williamson, IV | A61B 17/083 |
| 10,660,643 B2 | 5/2020 | Kubiak et al. | |
| 11,013,518 B2* | 5/2021 | Zhong | A61B 17/10 |
| 11,046,747 B2 | 6/2021 | Wong et al. | |
| 2005/0216036 A1 | 9/2005 | Nakao | |
| 2005/0234297 A1 | 10/2005 | Devierre et al. | |
| 2006/0235457 A1 | 10/2006 | Belson | |
| 2007/0213747 A1 | 9/2007 | Monassevitch | |
| 2007/0219571 A1 | 9/2007 | Balbierz | |
| 2007/0270644 A1 | 11/2007 | Goldfarb et al. | |
| 2008/0214893 A1 | 9/2008 | Tartaglia et al. | |
| 2010/0010511 A1 | 1/2010 | Harris et al. | |
| 2012/0059400 A1 | 3/2012 | Williamson | |
| 2012/0095480 A1 | 4/2012 | Jugenheimer et al. | |
| 2012/0245693 A1 | 9/2012 | Gorek | |
| 2015/0257757 A1 | 9/2015 | Powers et al. | |
| 2016/0192996 A1 | 7/2016 | Spivey et al. | |
| 2017/0105726 A1 | 4/2017 | Smith et al. | |
| 2018/0206711 A1 | 7/2018 | Piskun | |
| 2019/0167075 A1 | 6/2019 | Fischer et al. | |
| 2020/0315436 A1 | 10/2020 | Pansky et al. | |
| 2020/0397445 A1* | 12/2020 | Shikhman | A61B 17/1285 |

OTHER PUBLICATIONS

International Search Report And Written Opinion PCT/US18/67432 Dated 06.25.2019.
International Search Report And Written Opinion PCT/US21/53685 dated Feb. 3, 2022.

* cited by examiner

Detail A

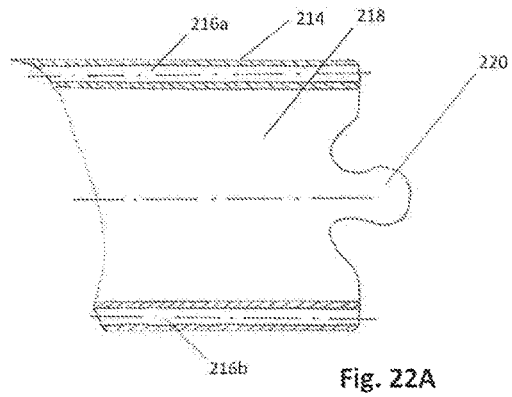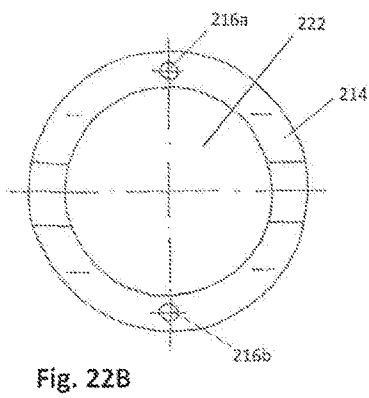
Fig. 22A    Fig. 22B
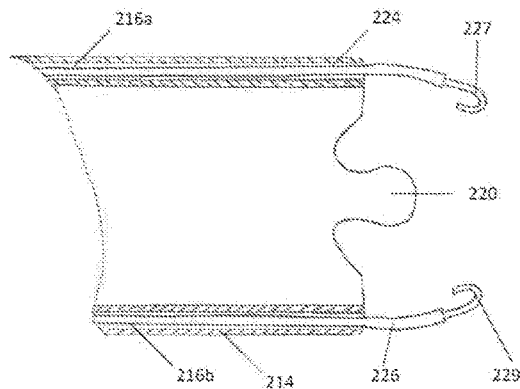
Fig. 23A
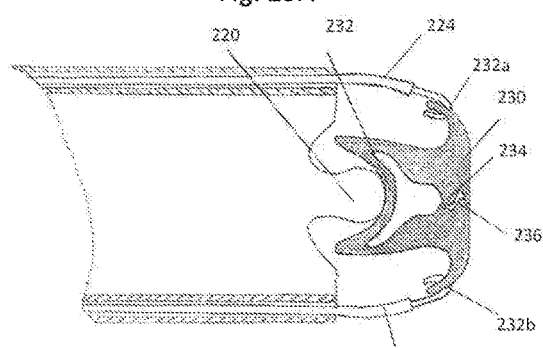
Fig. 23B

SURGICAL CLIP AND DEPLOYMENT SYSTEM

This application is a 371 of International PCT/US18/67432, filed on Dec. 23, 2018, which claims priority to provisional application 62/613,902, filed Jan. 5, 2018, provisional application 62/648,586, filed Mar. 27, 2018, and provisional application 62/648,593, filed Mar. 27, 2018. The entire contents of each of these applications are incorporated herein by reference.

BACKGROUND OF THE INVENTION

1. Field of the Invention

This application relates to a surgical clip and a system and method for deploying the surgical clip to compress tissue.

2. Background of the Related Art

Clips for closing defects in the GI tract are known. In one approach, clips are inserted through a working channel in an endoscope. However, this approach has the disadvantage of the size of the clip being limited since it must be dimensioned to fit through the small dimensioned working channel of the scope. Additionally, the instrument for delivering the clip must also be of small diameter since it also has to fit through the working channel. If the clip delivery instrument has jaws, the range of the jaws is limited due to the size limitations of the working channel. With the size restrictions, the clip in certain applications is unable to fully clamp the vessel or tissue, resulting in insufficient tissue clamping and/or requiring multiple clips to be applied which adds to the time and complexity of the surgical procedure.

In another approach, disclosed in U.S. Pat. No. 6,428,548, a clip is provided with opposing grasping surfaces and joints connecting the ends of the grasping surfaces. The clip is placed on an outer surface of an endoscope cap with the cap applying a force that retains the clip in the tissue receiving (open) position. To apply the clip to tissue, the clip is deployed off of the endoscope cap so the force is no longer applied against the grasping surface so the joints due to their stored potential energy return the grasping surfaces to the grasping position to compress tissue between the grasping surfaces. This approach also has several disadvantages. First, there is no controlled opening or closure of the clip since the clip is biased open by the endoscope cap and springs back to a closed position when deployed off the cap. Second, due to the positioning of the clip, visualization is compromised. Third, once the clip is released onto tissue, it cannot be re-opened and repositioned.

The need therefore exists for a compression clip and delivery system for closing defects in the GI tract, as well as for other clinical applications, that are of sufficient size, enable controlled opening and/or closing of the clip, improve visibility so the clinician can ensure proper tissue apposition, retraction and clip application and can be re-opened and positioned if the clinician determines that the initial positioning of the clip is not desirable.

SUMMARY

The present invention overcomes the problems and deficiencies of the prior art. The present invention advantageously provides a clip for compressing tissue which can be controllably moved to the open position. The clip can also in some embodiments be controllably moved to the closed position. The clip can further advantageously be removed and repositioned after placement on body tissue. The present invention also provides a system and method for delivering the clip which is easily mountable over an endoscope and provides controlled manipulation.

In accordance with one aspect of the present invention, a system for compressing body tissue is provided comprising a surgical clip having at least a first tissue contacting surface and at least a second tissue contacting surface. The clip is movable from a closed position to an open position, wherein in the open position the clip receives tissue between the first and second tissue contacting surfaces and in the closed position the clip compresses tissue between the first and second tissue contacting surfaces. A clip deployment device is provided having a first clip engagement member and a second clip engagement member engageable with the clip, the first and second clip engagement members movable between first and second positions to controllably move the clip from the closed position to the open position.

In some embodiments, the first and second clip engagement members are movable independently.

In some embodiments, the clip is radially expandable from a closed position to an open position.

In some embodiments, the clip is normally in the closed position and the first and second engagement members apply a force to different sides of the clip to open the clip from the closed position and release returns it to a closed position. In other embodiments, the clip is deformable so it is forced to an open position and forced to a closed position.

In some embodiments, the first tissue contacting surface has a first plurality of teeth and the second tissue contacting surface has a second plurality of teeth, and the first tissue contacting surface is on a first side of the clip and the second tissue contacting surface is on a second side of the clip, and the first engagement member engages the first side of the clip and the second engagement member engages the second side of the clip.

In some embodiments, the clip deployment device comprises a sheath and the first and second engagement members extend through the sheath, the sheath configured for mounting over an endoscope and the clip mounted on the sheath.

In some embodiments, the clip is mounted on the sheath facing distally, wherein movement of one of the engagement members changes the orientation of the clip to an angle to a longitudinal axis of the sheath.

In accordance with another aspect of the present invention, a system for compressing body tissue is provided comprising a surgical clip having a first tissue contacting surface and a second tissue contacting surface, the clip movable from a closed position to an expanded open position. In the open position, the clip receives tissue between the first and second tissue contacting surfaces and in the closed position the clip compresses tissue between the first and second tissue contacting surfaces. A clip deployment device has a sheath and a first clip engagement member and a second clip engagement member. The sheath is mountable over at least a distal portion of an endoscope so the scope is slidable within the sheath, the first and second clip engagement members engageable with the clip and slidable with respect to sheath to effect opening of the clip.

In some embodiments, the sheath has a first channel to receive the first engagement member and a second channel to receive the second engagement member.

In some embodiments, the clip is radially expandable so that movement of the first and second engagement members spreads first and second sides of clip away from each other to open the clip. In some embodiments, the clip is biased to the closed position and the first and second engagement members apply a force to first and second sides of the clip to force to the clip to the open position, wherein release of the force returns the clip to its normally closed position.

In accordance with another aspect of the present invention, a system for compressing body tissue is provided comprising a surgical clip having a first tissue contacting surface and a second tissue contacting surface, the clip movable from a closed position to an open position. In the open position, the clip receives tissue between the first and second tissue contacting surfaces and in the closed position the clip compresses tissue between the first and second tissue contacting surfaces. A clip deployment device is provided having a longitudinal axis, a first clip engagement member and a second clip engagement member axially spaced from the first clip engagement member. The clip is mounted to the deployment device in a lateral orientation so the first tissue contacting surface is axially spaced from the second tissue contacting surface, wherein movement of the second clip engagement member in an axial direction moves the second tissue contacting surface axially away from the first tissue contacting surface to move the clip to the open position.

In some embodiments, the first clip engagement member remains stationary as the second clip engagement member is retracted in an axial direction. In some embodiments, the second tissue contacting surface is proximal of the first tissue contacting surface when the clip is mounted to the deployment device. In some embodiments, the clip is normally in a closed position.

In some embodiments, the clip deployment device includes a sheath, the sheath mountable to an endoscope.

In accordance with another aspect of the present invention, a system for compressing body tissue is provided comprising a surgical clip having a first tissue contacting surface and a second tissue contacting surface, the clip movable from a closed position wherein the first and second tissue contacting surfaces are facing toward each other to an open position wherein the first and second tissue contacting surfaces are pivoted away from each other. The clip has a first receiving portion on a first side of the clip and a second receiving portion on a second side of the clip, the first tissue contacting surface being on the first side and the second tissue contacting surface being on the second side. A clip deployment device has a first clip engagement member and a second clip engagement member, the first clip engagement member engageable with the first receiving portion and a second clip engagement member engageable with the second receiving portion. The first clip engagement member and second clip engagement member can be movable between first and second positions to controllably pivot the clip from the closed position to the open position.

In some embodiments, the first and second clip engagement members are movable independently.

In some embodiments, the clip is normally in the closed position and is forced open by movement of the first and second clip engagement members. In some embodiments, the first tissue contacting surface has a first plurality of teeth and the second tissue contacting surface has a second plurality of teeth for compressing tissue.

In some embodiments, the clip is normally in the closed position and the first and second engagement members apply a force to the first and second sides of the clip to force the clip to the open position, wherein release of the force returns the clip to its normally closed position. In other embodiments, the clip is deformable to the closed position.

In some embodiments, movement of one of the first and second engagement members changes the orientation of the clip to an angle to a longitudinal axis of the clip deployment device.

In some embodiments, the clip deployment device includes a sheath mountable to at least a distal portion of the endoscope.

In accordance with another aspect of the present invention, a surgical clip for compressing body tissue is provided comprising a first tissue contacting surface and a second tissue contacting surface, the clip being movable from a normally closed position wherein the first and second tissue contacting surfaces are facing each other to a radially expanded open position wherein the first and second tissue contacting surfaces are moved away from each other. The clip has a first receiving portion on a first side of the clip and a second receiving portion on a second side of the clip, the first tissue contacting surface being on the first side and the second tissue contacting surface being on the second side. The first receiving portion is dimensioned to receive a first movable clip opening member and the second receiving portion dimensioned to receive a second clip opening member for moving the clip between open and closed positions.

In some embodiments, the first and second tissue contacting surfaces comprise a non linear surface for applying a compressive force to tissue.

In some embodiments, the first and second receiving portions are at a central region of the clip; in other embodiments the first and second receiving portions are at end regions of the clip. When the receiving portions are at end regions, in some embodiments, a compressive force can be applied.

In accordance with another aspect of the present invention, a sheath mountable over at least a distal end of the endoscope is provided comprising a first channel, a second channel, a first clip engagement member and a second clip engagement member. A first actuator is slidable in the first channel, wherein movement of the first actuator moves the first clip engagement member to open a first side of a surgical clip mountable to the sheath. A second actuator is slidable in the second channel, wherein movement of the second actuator moves the second clip engagement member to open a second side of the surgical clip mountable to the sheath.

In accordance with another aspect of the present invention, a method of applying a surgical clip to tissue to apply a compressive force to tissue is provided comprising the steps of:

moving a first clip engagement member and a second clip engagement to apply a force to first and second sides of the clip to move the clip from a closed position to an open position, the clip carried by a sheath mounted over an endoscope;

advancing an endoscope to view target tissue;

retracting the endoscope proximally within the sheath;

advancing a tissue retractor though the open clip to approximate and retract tissue into the space between first and second tissue contacting surfaces of the clip; and moving the first and second clip engagement members to release the clip to return to the closed position.

In some embodiments, the method further comprises the step of retracting the sheath to increase the field of vision of the endoscope. In some embodiments, the endoscope can be advanced through the opening in the open clip.

In some embodiments, the clip can be removed from the tissue and reapplied after the clip is closed on tissue. In some embodiments, the clip can be removed by moving the first clip engagement member and the second clip engagement to apply the force to first and second sides of the clip to move the clip from a closed position to an open position.

In some embodiments, advancement of one of the clip engagement members orients the clip to an angle to a longitudinal axis of the sheath.

In some embodiments, the first and second clip engagement members are independently movable.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIGS. 10A and 10B illustrate one method of deployment of the clip of FIG. 9A wherein FIG. 10A is a side view of the clip in its normally closed position engaged with the hooks of the delivery system and FIG. 10B is a cross-sectional view similar to FIG. 10A illustrating advancement of the tubular members to force the links radially outwardly to expand the clip radially outwardly to the open position, the sheath of the clip deployment system shown in cross-section;

FIG. 22A is a cross-sectional view of the delivery sheath of an embodiment of the present invention;

FIG. 22B is a front view of the delivery sheath of FIG. 22A;

FIG. 23A is a view similar to FIG. 22A showing the flexible links and engagement hooks for manipulating the surgical clip;

FIG. 23B is a view similar to FIG. 23A showing a surgical clip of an alternate embodiment resting on the hinge support and engaged by the hooks of the deployment system;

FIGS. 40 and 41 are perspective views of an alternate embodiment of the clip deployment system for lateral orientation of the clip, wherein FIG. 40 illustrates the clip in the closed position and FIG. 41 illustrates the proximal hooks retracted to move the clip to the open condition;

DETAILED DESCRIPTION OF PREFERRED EMBODIMENTS

Figure 1A:
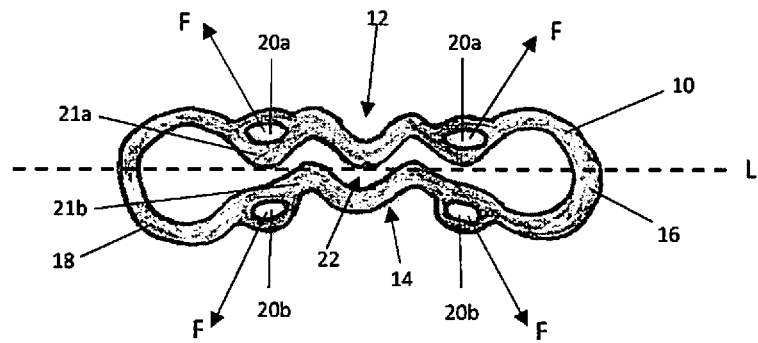
FIG. 1A is a front view of a first embodiment of the radially expandable surgical clip of the present invention shown in the relaxed closed condition (state)

The present invention provides a system and method for closure of wall defects in the hollow organs, such as a colon, esophagus, stomach etc. The system includes a surgical clip and a deployment device for delivering the surgical clip to tissue and manipulating the clip between closed and open positions by applying a force to opposing sides of the clip. In one approach/aspect, the clips of the present invention are radially expandable from a closed position to an open position to enable tissue to be positioned within an opening in the clip, and then returnable to the closed position to compress tissue between opposing compression surfaces or points of the clip. Various embodiments of the radially expandable clips are discussed in detail below. The opening of the clips is controlled by a clip deployment device which has clip engagement members actuable by the clinician outside the patient, such actuation applying a force to opposing sides of the clip to spread the tissue contacting surfaces of the clip apart. The control of the clip enables the clip to be reopened and repositioned if necessary during the surgical procedure. The clip engagement members additionally allow for controlled, e.g., incremental, closure (and/or opening) of the clip if desired. Various embodiments of the clip deployment device are discussed in detail below in conjunction with the method of use.

The clips of the present invention are delivered by an endoscope as the clip deployment device is in the form of a sheath or cap placed over an endoscope. In this manner, the clips of the present invention can be delivered by a conventional endoscope. The sheath includes and/or supports the clip engagement members for clip manipulation as described below.

Thus, the delivery device of the present invention is able to open or close the clip on demand allowing the user to control its deployment. The clip could be closed over the target tissue slowly and gently to minimize unnecessary tissue damage due to over compression. The clip can be deformable or normally in a closed position. The user can visually confirm that the clip captures tissue appropriately and circumferentially before the delivery device is disconnected leaving the clip in place. If necessary, the user can re-open and reposition the clip if its location is not satisfactory. The clip is configured to allow an engagement with the clip actuating members, e.g., links or jaws of the delivery system. The actuating members can in some embodiments be operated independently to apply a force to a side of the clip that it is connected to. After the clip is delivered and its proper placement is confirmed, the actuating members are disengaged. In some embodiments, the force could be applied to just one side of the clip, while the other side is held stationary or substantially stationary (minimal movement). Alternatively, the force could be applied to both sides either simultaneously or one side at the time.

In an alternative approach/aspect to the radially expandable clips wherein two sides of the clip are spread apart to open the clip, several embodiments of a hinged clip are disclosed. With the hinged clip, the clip is opened by pivoting one or both sides of the clip about a hinge to an open position where the tissue engaging surfaces on each side of the clip are pivoted away from each other in opposing directions, and then pivoted back toward each other to the closed position to compress tissue placed within an opening in the open clip. Various embodiments of the hinged clip are discussed in detail below. As with the radially expandable clips, the hinged clips are delivered by a clip deployment device which is mounted over a conventional endoscope, and clip actuating members control opening and closing of the clip. Various mechanisms for opening and closing the hinged clip are disclosed, which enable repositioning of the clip if desired after placement. Closure of the clip can be controlled. The clip can be normally closed or deformable to a closed position.

Turning now to the drawings wherein like reference numerals identify similar structural features of the devices disclosed herein, there are illustrated several embodiments of the radially expandable clip in FIGS. 1-9B. In these embodiments, the clip is a normally closed spring-like component, although alternatively as in the other clips disclosed herein, the clip could be in a non-spring form so it is deformed to open and deformed to close. The clips (as well as the other clips disclosed herein) are preferably made out of a super-elastic material such as Nitinol, although other materials are also contemplated. The clip is opened mechanically by applying a force to its opposite sides, the force applied by the clip delivery device. The clip is deformed under this force as it expands in a generally radial direction, i.e., the opposing tissue contacting surfaces are spread away from each other.

Figure 1B:
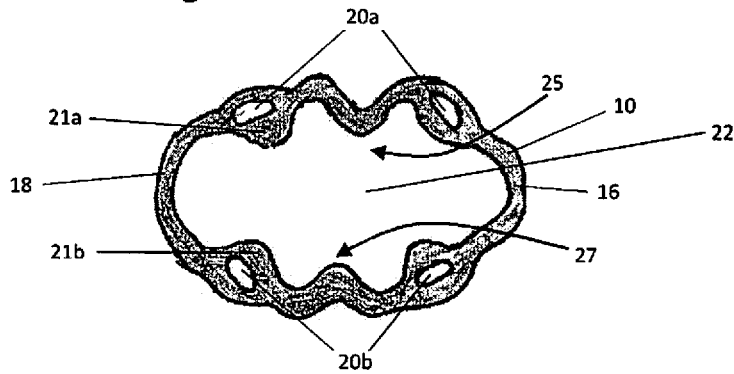
FIG. 1B is a front view of the surgical clip of FIG. 1A in the radially expanded (open) condition (state) after a force is applied.

Turning first to FIGS. 1A and 1B, a first embodiment of the clip of the present invention is illustrated, designated generally by reference numeral 10. Clip 10 is shown in its normally closed position (condition or state) in FIGS. 1A and 1n its open position (condition or state) in FIG. 1B. Note the terms "closed position," "closed state" and "closed condition" are used interchangeably herein and the terms "open position", "open state" and "open condition" are also used interchangeably herein.

Note as used herein, the term distal refers to further from the clinician and the term proximal refers to closer to the user. Thus, the clip deployment system is inserted in a distal direction to the target site.

Clip 10 can have a closed geometric shape with opposing loops 16, 18 at its ends (sides). Imaginary line L which bisects the clip 10 into two sides is shown for ease of explanation as clip 10 has a first side 12 and an opposing side 14. Side 12 includes a tissue contacting surface 25 (also referred to as a tissue engaging surface) having a plurality of teeth 21a and side 14 has a tissue contacting surface 27 (also referred to as a tissue engaging surface) having a plurality of teeth 21b. (Only one of the teeth on each side is labeled for clarity in this Figure as well as the other Figures illustrating alternate embodiments). The tissue contacting surfaces 25, 27 face each other in this relaxed closed position of the clip 10 so the teeth 21a 21b either partially or fully intermesh. The teeth 21a, 21b provide a tissue compression surface (tissue compression points) to compress tissue between the opposing tissue contacting surfaces 25, 27 when the clip is in the closed position. Note that the tissue contacting surfaces preferably provide an irregular, i.e., a non-linear surface such as a wavy surface, which can be in the form of teeth as shown to provide the tissue compression points to create tissue compression surfaces, however, they could also be in form other than teeth to provide tissue compression surfaces. The tissue compressing surfaces could also alternatively be flat or curved. Note that in the closed position, the teeth preferably intermesh so that the imaginary line L would pass through a portion of teeth 21a, 21b. However, it should be appreciated that the degree of crossing the imaginary line, and even crossing of the imaginary line, will depend on the tissue thickness. This is also the case with the other embodiments of the clip discussed below. Note that multiple tissue contacting surfaces can be provided.

When the first and second sides 12 and 14 of clip 10 are spread, i.e., radially expanded, by the clip deployment actuators described below, the space 22 between the two sides 12, 14 is increased as shown in FIG. 1B to provide a space for placement of tissue between the tissue contacting surfaces 25, 27. In this open position, the tissue contacting surfaces 25, 27 are still facing (or substantially facing) each other but are further apart. Note that preferably the clip is spread in a single plane but it is also understood that deformation of the clip might in certain instances result in deformation slightly out of the plane, however, the tissue contacting surfaces 25, 27 would still substantially face each other, even if slightly angled. In alternate embodiments, instead of the clip being flat, it could be curved shape which could in some instances can better conform to the cylindrically shaped colon. It could be curved during manufacture. Also, since the clip is flexible, it could flex and comply with tissue curvature after it is deployed.

Clip 10 has a pair of openings 20a on first side 12 and a pair of openings 20b on the second side 14. These openings 20a, 20b are shown spaced apart and spaced from a center of the clip 10. These openings 20a, 20b provide one form of receiving portions as they are engaged by the clip engagement members of the delivery system described in detail below. The clip engagement members apply forces F at the openings 20a, 20b in opposing directions to expand the clip radially. Thus, under the load of the force F that is applied to the openings 20a and 20b, the clip expands radially creating a tissue opening 22. The target tissue is retracted into this opening 22, and the clip 10 is closed to compress the tissue.

Figure 6A:
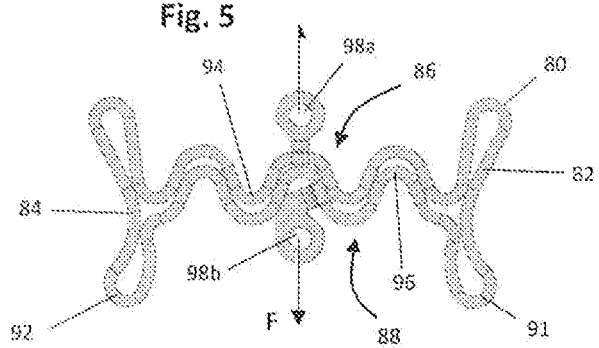
FIG. 6A is a front view of another alternate embodiment of the surgical clip of the present invention shown in the relaxed closed condition.
Figure 6B:
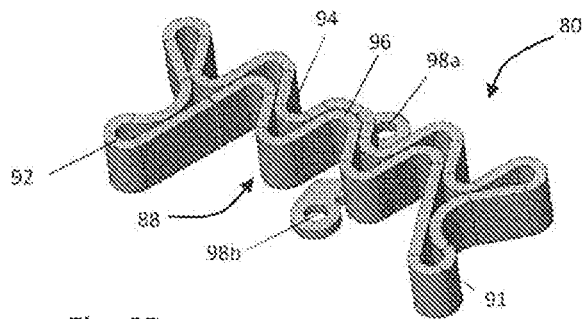
FIG. 6B is an isometric view of the clip of FIG. 6A.

FIGS. 6A and 6B illustrate an alternate embodiment of the clip of the present invention. Clip 80 has a first side 86 with a first tissue contacting surface having a plurality of teeth 94 and a second side 88 with a second tissue contacting surface having plurality of teeth 96. The teeth 94, 96 can partially intermesh or fully mesh as shown in the closed position (condition) of FIG. 6A. As with teeth 21a and 21b of clip 10 of FIG. 1A, the teeth provide compression points or surfaces for compressing tissue between the opposing tissue contacting surfaces. Clip 80, rather than having a pair of openings on each side for clip engagement members as in FIG. 1A, has a single opening 98a, 98b on each side 86, 88 respectively. As shown, the openings 98a, 98b can be positioned at the center of each side 86, 88. The openings 98a, 98b are in the form of eyelets extending from a post projecting radially. The clip 80 has a closed geometric shape with ends 82, 84 having larger loops 91, 92. Clip 80 can be formed from a laser cut tube, a ribbon, sheet metal, round or rectangular wire, etc. In a preferred embodiment, clip 80 is formed from a ribbon of a super-elastic material such as Nitinol, although other materials are also contemplated. The ends of the ribbon or wire are attached to each other, for example, by welding.

Figure 7A:
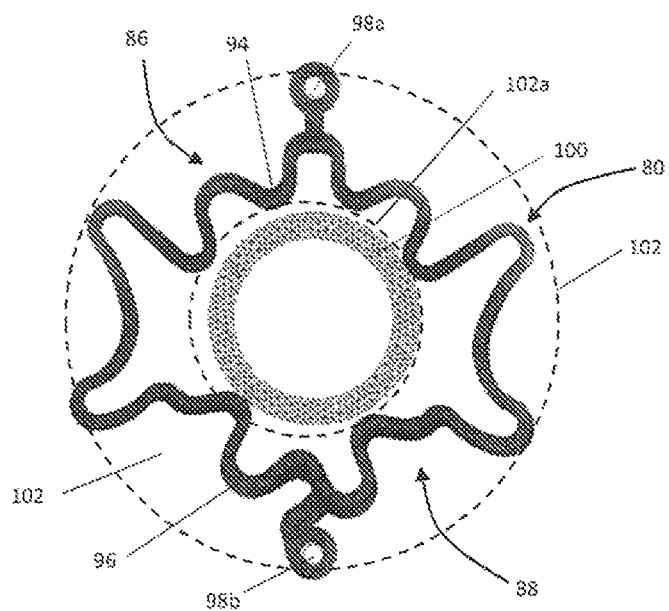
FIG. 7A is a front view of the clip of FIG. 6A shown in relation to the endoscope and shown in the expanded (open) position to enable tissue to be introduced between the compression surfaces of the clip.
Figure 7B:
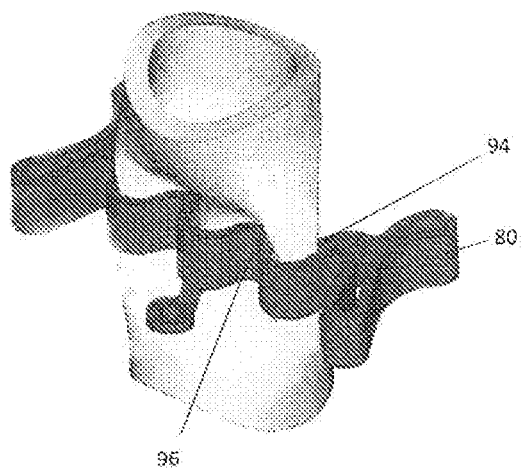
FIG. 7B is a perspective view illustrating the clip of FIG. 6A in the closed position compressing tissue between the compression surfaces.

FIG. 7A illustrates the clip 80 in an open position, after force F is applied by clip engagement members of the delivery system at the region of openings 98a, 98b to radially expand the clip from its relaxed closed state (position). FIG. 7A also illustrates the clip positioned on sheath 102 of the delivery system that is positioned over an endoscope 100, which are discussed in more detail below in conjunction with the clip deployment system and method. The length of the clip 80 (defined as the longest dimension of the clip, i.e., from one edge of the clip to the opposite edge) can slightly exceed the diameter of the sheath 102 as in FIG. 7A, or alternatively, can be dimensioned to be the same diameter or less than the diameter of the sheath (see e.g. FIG. 9A) so it is does not extend past the outer dimension of the sheath during delivery. After force F is applied to both sides 86, 88 of the clip to open the clip (see the arrows of FIG. 6A), tissue is positioned in the opened space between the opposing tissue contacting surfaces on sides 86, 88, and then the force is released so the clip 80 can return to its normal closed position of FIG. 7B to compress tissue between the teeth 94, 96.

Figure 8:
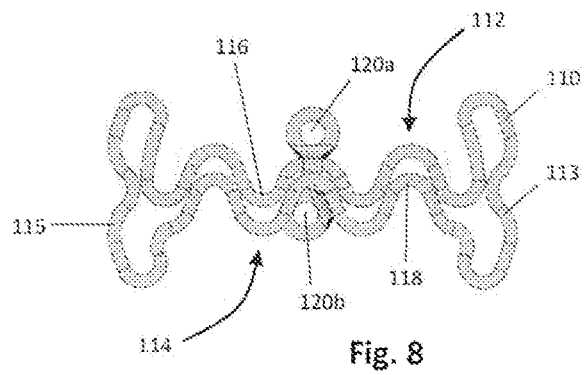
FIG. 8 is a front view of another alternate embodiment of the surgical clip of the present invention shown in the relaxed closed condition.

The clip 110 of the alternative embodiment of FIG. 8 is similar to the ribbon form (or flat stock form) clip of FIG. 6A except for the looped end regions 113, 115. Otherwise, clip 110 is the same as clip 80 in configuration and in function as it has opposing sides 112, 114 with opposing tissue contacting surfaces having teeth 116 and 118 and openings 120a, 120b engaged by clip engaging members to applying opposing forces to sides 112, 114 to open, i.e., spread, the clip from its normally closed position to an open position to receive tissue.

Figure 4:
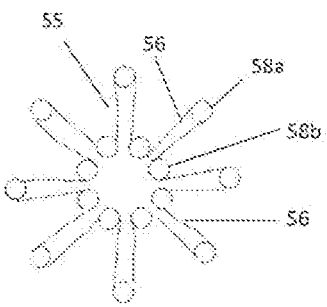
FIG. 4 is a front view of another alternate embodiment of the surgical clip of the present invention shown in the relaxed closed condition.
Figure 5:
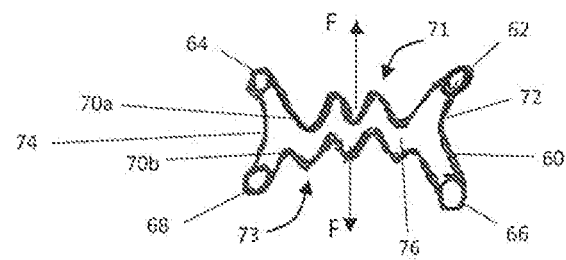
FIG. 5 is a front view of another alternate embodiment of the surgical clip of the present invention shown in the relaxed closed condition.

The foregoing describes clips formed from flat stock, e.g., metal sheet, ribbon, etc. by way of example. In the alternate embodiments of FIGS. 3-5, the clip is formed from a single wire. In FIG. 5, clip 60 has a closed geometric shape with a first side 71, a second side 73 and two looped sides 72, 74. Tissue contacting surfaces on first side 71 and second side 73 have a series of teeth 70a, 70b, respectively. Openings 62, 64 on first side 71 and openings 66, 68 on second side 73 are engaged by clip engaging members of the deployment device to apply opposing forces to sides 71, 73 to open, i.e., spread, the clip 60 from its normally closed position for receipt of tissue in space 76, and the clip 60 is subsequently released to return to its closed condition to compress tissue between the tissue contacting surfaces. Openings 62, 64, 66 and 68 are in the coils in the sides of the clip. That is, clip 60 can be formed from a single wire which is formed into four coils at 62, 64, 66 and 68.

Figure 3:
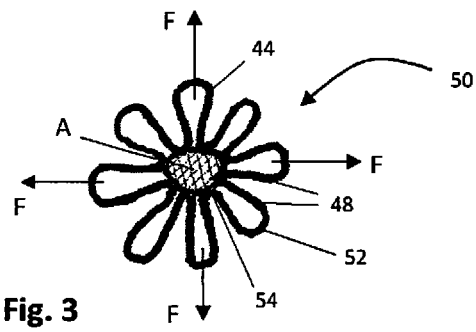
FIG. 3 is a front view of another alternate embodiment of the surgical clip of the present invention shown in the relaxed closed condition.

In the embodiment of FIG. 3, the clip 50 is formed of a single wire in a flower shape with a plurality of petals 48. The clip 50 is configured to compress tissue A when the clip is in the closed position as the teeth 54 at the bottom of each petal 48 engage the tissue. Forces F are applied to expand the clip 50 from its normally closed position of FIG. 3 in the four directions shown by the arrows and allow tissue to be retracted into the space between the teeth, and then the clip 50 is released to return to its closed position shown in FIG. 3 to compress the tissue between the teeth. In the embodiment of FIG. 4, the clip 55 is formed from a single wire into a closed shape in a flower like form. Clip 55 is formed into a series of loops, e.g., petals. Petals 56 are formed into a coil 58a at the top (outer region) of the petal 56. A coil 58b is formed at a bottom (inner region) between each petal 56, Stated another way, the wire of clip 55 is formed so that one leg of the first petal extends radially outwardly and forms into a first outer coil at its outward (top) end which then extends inwardly to form a second leg of the first petal which then at the bottom (inner end) forms a first lower coil which then extends radially outwardly to form the first leg of the second petal where it forms a second outer coil at the top and then extends downwardly to form the second leg of the second petal to then form at the bottom a second inner coil, and so forth. The coils provide the compressive force against tissue as an alternative to the teeth described in the foregoing embodiments. To open the clip 55, a select number of opposing outer coils 58a are engaged by clip engaging members to applying opposing forces (as in FIG. 3) to expand (spread) the clip 55 from its normally closed position in several directions, e.g., four directions, and allow tissue to be retracted into the space between the bottom (inner) coils, and then the clip 55 is released to return to its closed position shown in FIG. 4.

Figure 2:
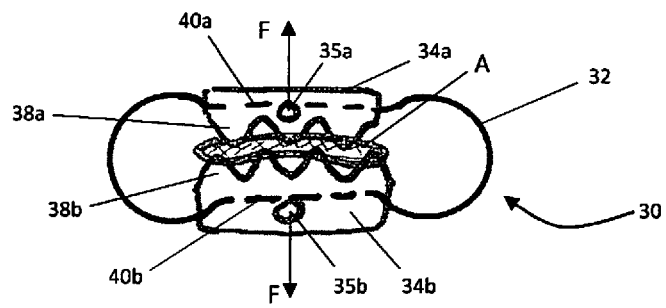
FIG. 2 is a front view of an alternate embodiment of the surgical clip of the present invention shown in the relaxed closed condition (state)

In the embodiment of FIG. 2, clip 30 has a wire-form that creates a tissue compression force. Elements 34a and 34b are attached to the opposite sections of the wire 32, e.g., the wire can extend through channels 40a, 40b in the elements 34a, 34b. The elements 34a, 34b have tissue contacting surfaces 38a, 38b in the form of teeth that compress tissue A when the clip 30 is in the closed position. The elements 34a, 34b further have openings 35a, 35b to receive clip engagement members of the delivery system, to which the forces F are applied to move (radially expand) the clip 30 into the open position. The wire 31 functions as a spring to bias the elements 34a, 34b toward each other.

The system and method of deployment of the radially expandable clip will now be described in conjunction with FIGS. 10A-20. The deployment method is illustrated and described for application of radially expandable clip 120 of FIGS. 9A, 9B, however, it should be understood that the other clips disclosed herein, e.g., the radially expandable clips of FIGS. 1-8 and the hinged clips of FIGS. 21-29, of FIGS. 1-8 can also be deployed and manipulated in the same manner, i.e., mounted to the sheath, engaged by clip engagement members, actuated so the clip engagement members open the clip, etc.

Clip 120 is similar to clip 10 of FIG. 1A except instead of two openings for the clip engagement members on each side of the clip, a single opening 125a, 125b is provided of each side. Clip 120 has a first side 122 having a tissue contacting (engaging) surface 131 with a plurality of teeth 130 and a second side 124 with a tissue contacting (engaging) surface 133 with a plurality of teeth 132. Clip 120 has a closed geometric shape with end loops 126, 128. Clip 120 is shown in the closed position in FIG. 9A mounted on sheath 140 and in an open position in FIG. 9B wherein sides 122, 124 are spread apart by application of force via openings 125a, 125b to open the space 134 between the opposing tissue contacting surfaces 131, 133. Clip 120 in this embodiment is shown within the confines of the sheath diameter, i.e., in the closed and open (expanded) position it does not exceed the diameter of the sheath 140. However, as noted above, in alternate embodiments, the clip 120 can exceed the sheath diameter.

Figure 10A:
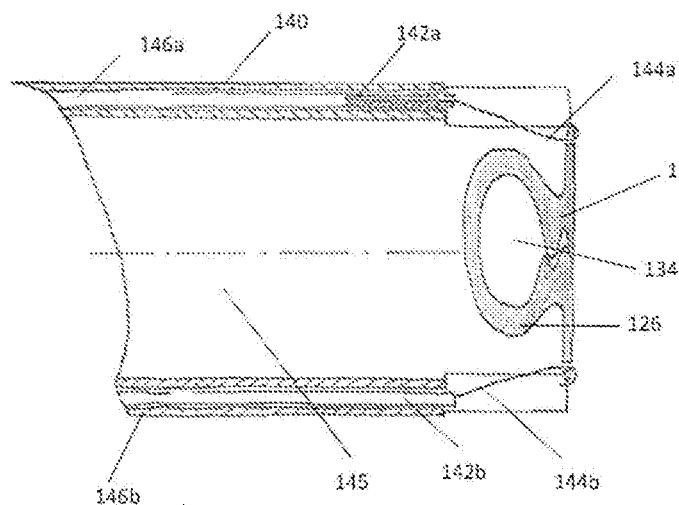
Figure 9A:
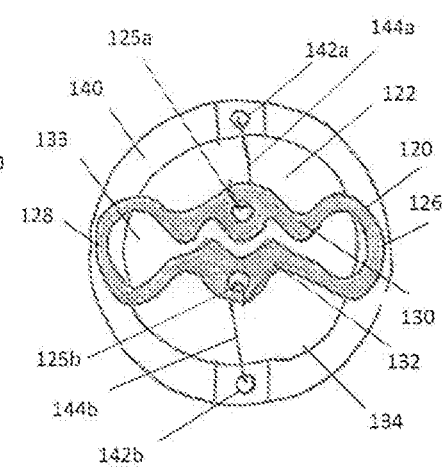
FIG. 9A is a front view of another alternate embodiment of the surgical clip of the present invention shown in the relaxed closed condition and mounted to a sheath.

Turning now to the method of applying the clip to tissue, FIG. 10A illustrates the clip 120 mounted to the sheath 140 in its normally closed position. The clip insertion and deployment device includes a sheath 140 having a first clip engagement member 144a in the form of a hook and a second clip engagement member 144b in the form of a hook. The hooks 144a, 144b extend through openings 125a, 125b of clip 120 to retain the clip 120 on the sheath 140. Slidable member 146a, e.g., rod or tube, slides within channel 148a of the sheath 140 and slidable member 146b, e.g., rod or tube, slides within channel 148b of sheath 140. Hook 144a is connected to tube 146a and hook 144b is connected to tube 146b so that movement of the tubes 146a, 146b effects movement of the respective hook 146a, 146b. The slidable rods 146a, 146b are actuated by the clinician outside the patient's body via control mechanism. Note the channels 148a, 148b can be formed in a wall of the sheath 140 as shown, or alternatively, can be separate channels formed outside of the outer wall of the sheath. The tubular members 142a, 142b are shown in the retracted position in FIG. 10A, and can slide forward within the channels 148a, 148b of the sheath 140. When slid forward, the tubular members 142a, 142b are advanced forcing the hooks (links) 144a and 144b to move radially outwardly as the hooks 144a, 144b move within the longitudinally aligned tubular members 142a, 142b. As a result, the clip 120 moves to its open position as the clip expands radially creating a tissue opening 134 as shown in FIG. 10B.

Sheath 140 has an opening or lumen (channel) to receive a flexible endoscope, colonoscope, laparoscope, etc. as the sheath 140 is configured and dimensioned to be positioned over an endoscope. Thus, the sheath 140 can includes a scope channel 145, preferably a center channel, and separate channels, radially spaced from the scope channel 145, for the actuators (manipulators) for controlling the clip 120. The sheath 140, as well as the other sheaths disclosed herein as alternate embodiments, can be positioned only over a distal region of the endoscope, over a more substantial region of the endoscope or over the entire endoscope. That is, the sheath can be in the form of a hollow sleeve placed over the entire scope or formed as an attachment to the distal end of the scope or only a portion of the scope. In preferred embodiments, the sheath 140, as well as the other sheaths disclosed herein, frictionally fits over the scope. In alternate embodiments, it can be clamped to the scope.

Alternatively, the delivery device (clip deployment device) could be implemented as a cap that is temporarily attached to the end of the scope and has manipulators to open and close the clip.

Figure 10B:
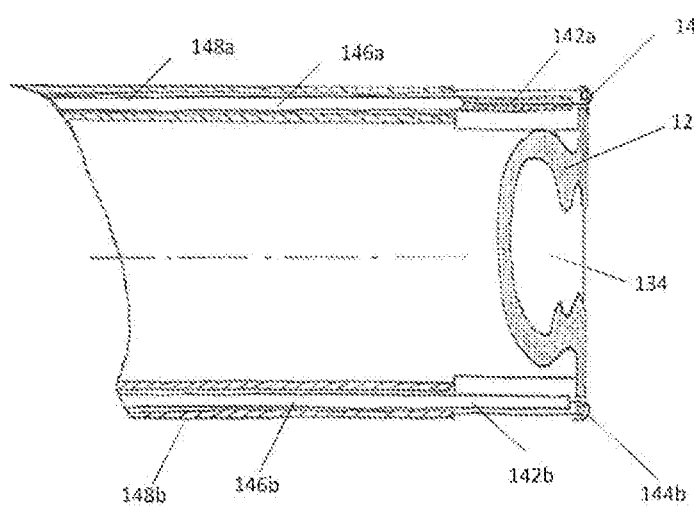
Figure 9B:
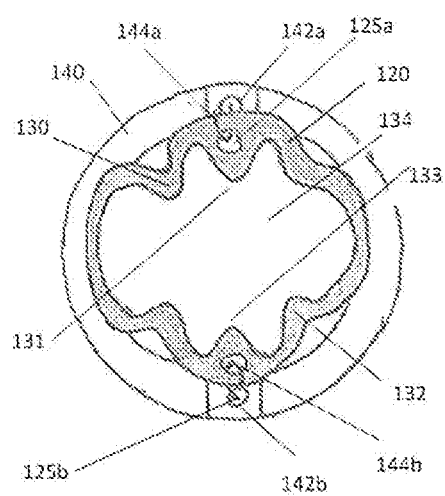
FIG. 9B is a front view of surgical clip of FIG. 9A shown in the tensioned open condition.
Figure 11:
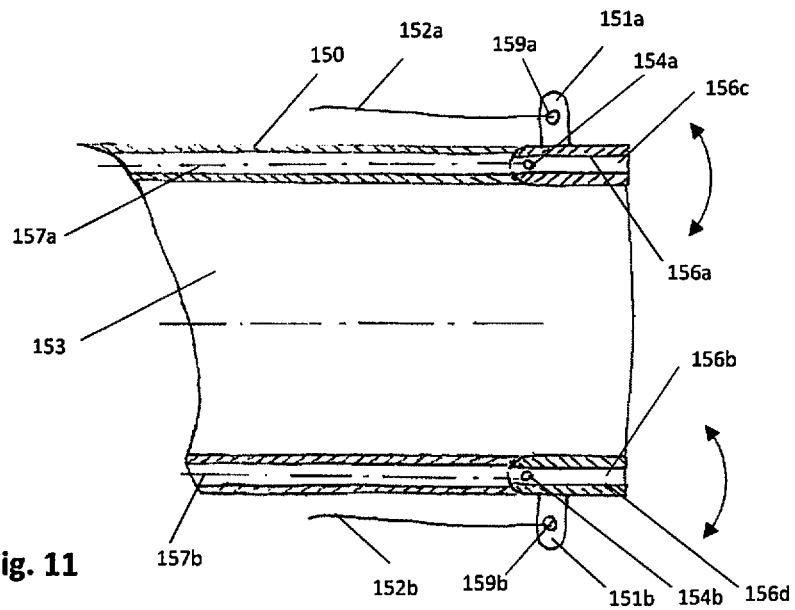
FIG. 11 is a side view of an alternate embodiment of the clip deployment system having rotatable links, the sheath of the clip deployment system shown in cross-section.

FIG. 10B illustrates the clip 120 and sheath 140 when the clip is manipulated to the open position by applying a force against its normal bias to the closed position. Elongated rods or tubes 146a, 146b, are movably axially within channels 148a, 148b of sheath 140. Being in the form of rigid tubular members, axial advancement of rods 146a, 146b changes the orientation of the more flexible hooks 144a, 144b to apply a force to the clip 120 as hooks 144a, 144b, positioned in openings 125a, 125b of clip 120, pull the opposing sides of the clip 120 apart to radially expand the clip 120 as the tissue contacting surfaces 131, 133 (and teeth 130, 132) are spread away from each other. This creates a space 134 for tissue so tissue can be positioned between the tissue contacting surfaces 131, 133 for closure of the clip 120 to compress the tissue. As can be appreciated, the manipulators/actuators enable opening and closing the clip on demand allowing the user to control its deployment. Thus, for example, the clip could be closed over the target tissue slowly and gently to minimize unnecessary tissue damage due to over compression.

Note tubes 142a, 142b can extend a length of the sheath 140 to connect to actuators at the proximal end. Alternatively, the tubes 142a, 142b can be smaller in length and pulled by a wire, rod or other elongated member which is connected to the actuators at the proximal region in a manner for example similar to FIG. 14C described below.

In the embodiment of FIGS. 10A and 10B, distal advancement of the tubular members 146a, 146b straightens the hooks 144a, 144b to expand the clip 120 to the open position. In the alternate embodiment of FIGS. 11 and 12, pivoting links are provided to effect opening of the clip. More specifically, sheath 150 can have two pivoting (rotatable) hubs 156a, 156b which rotate around pivots 154a and 154b. The hubs 156a, 156b can have outwardly projecting links 151a, 151b with openings 159a, 159b, respectively, which receive an actuator (manipulator) such as a wire 152a, 152b or alternatively another form of elongated member such as a rod or tube. When the push-pull link members 152a, 152b are actuated, the hubs 156a, 156b are pivoted about pivots 154a, 154b as illustrated by the arrows in FIG. 11. The hubs 156a, 156b can also have internal instrument channels 156c and 156d that are aligned with the sheath instrument channels 157a, 157b. Sheath 150, like sheath 140, has a channel 151 to receive a scope. The instrument channels 157a, 157b can be in the wall of the sheath 150 as shown or provided external the wall.

Figure 12:
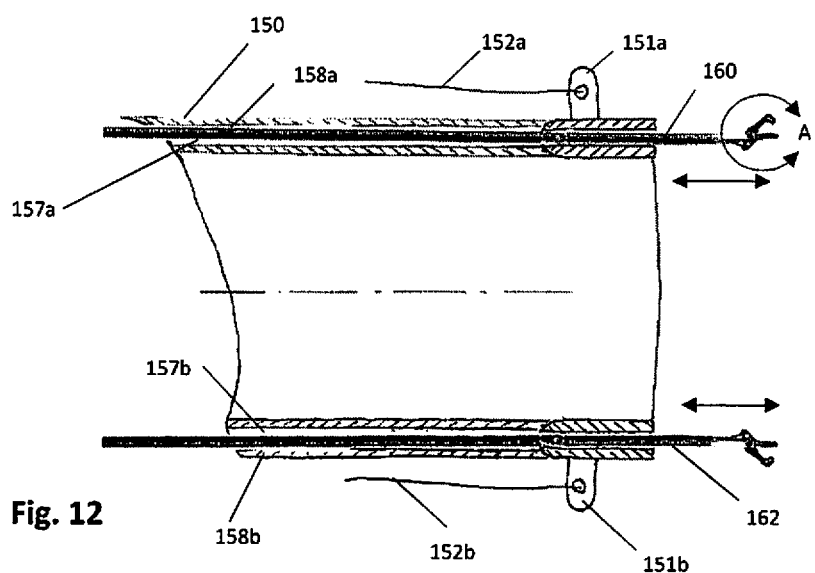
FIG. 12 is a side view of the deployment system of FIG. 11 showing insertion of clip engaging instruments through the sheath channels.
Figure 13:
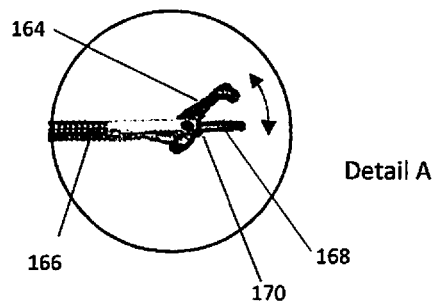
FIG. 13 is a close up view of the area of detail identified in FIG. 12.
Figure 14A:
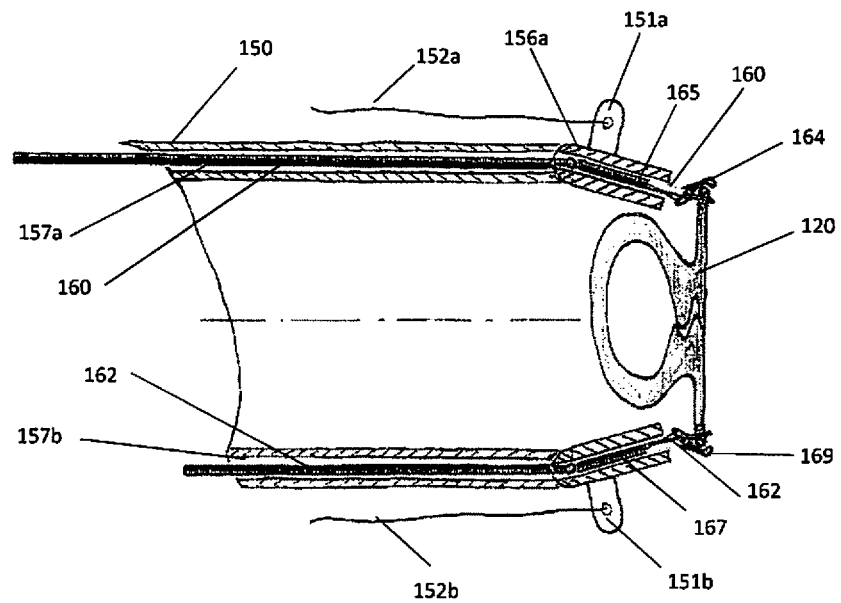
FIG. 14A is a side view similar to FIG. 11 showing the clip of FIG. 9A mounted to the sheath, the clip being in the normally closed position.
Figure 14B:
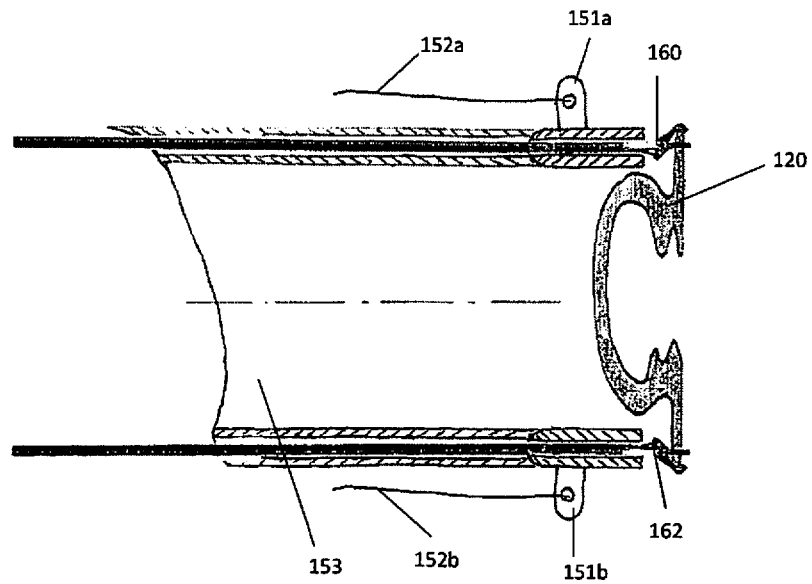
FIG. 14B is a side view similar to FIG. 14A showing a force applied to the links to expand the clip into the open condition (position) for receiving tissue.
Figure 14C:
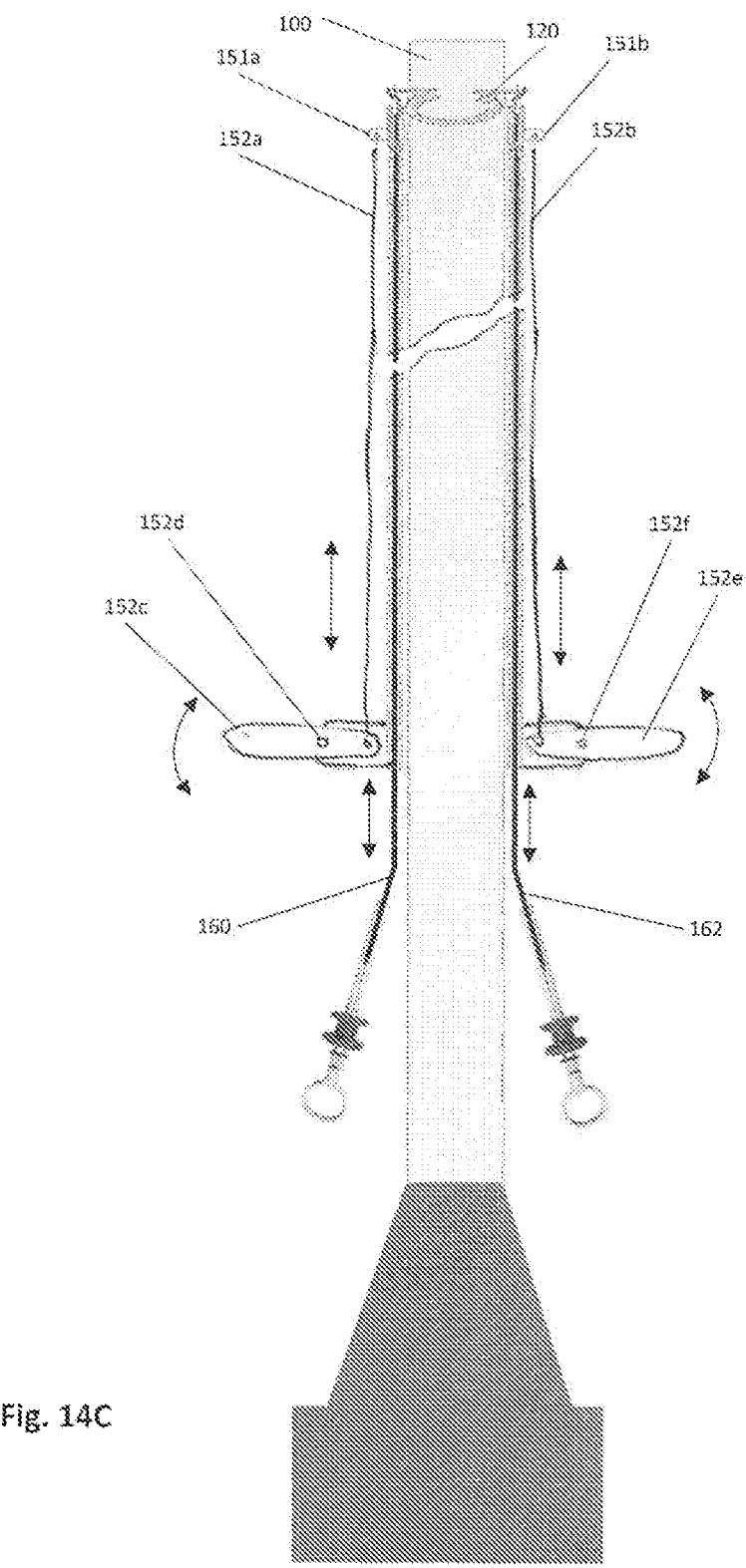
FIG. 14C is a side view showing the actuators for the clip engaging members of FIG. 14C.

Flexible instruments 160 and 162, or other clip engaging instrument, can be inserted into the instrument channels 157a and 157b of the sheath 150 and into and through the instrument channels 156c and 156d of the hubs 156a and 156b. The jaws of the instruments 160, 162 are configured to grasp opposing sides of the clip for manipulation thereof. With the hubs 156a, 156b in the angled position as shown in FIG. 14A, the flexible instrument shafts 165, 167 are bent radially inwardly at an angle to the longitudinal axis of the shaft to change the direction of the distal portion of the instruments 160, 162. In FIG. 12, the hubs 156a, 156b are in a linear, non-angled position, moving the instrument shafts 165, 167 to the linear or straight position. FIG. 14A illustrates the hubs 156a, 156b to an angled position when no force is applied to the elongated members 152a, 152b and thus the instruments shafts 165, 167 are angled Instrument 160 has a movable jaw 164 pivotably mounted to stationary jaw 168 to pivot about pivot 170 (FIG. 13) between open and closed positions. Instrument 162 similarly has a pivotable jaw 169 mounted to a stationary jaw to pivot between an open position and closed position. In the closed position of the jaws 164, 169, the clip 120 is grasped and retained as shown in FIG. 14A. In one embodiment, one stationary jaw extends through opening 125a (FIG. 9B) of clip 120 on one side of the clip 120 and the other stationary jaw extends though opening 125b on the opposing side of the clip 120. The pivotable jaw 164, 169 are manipulated to the closed position to grasp the clip 120, the jaws being actuated by a proximal actuator(s) outside the patient's body.

The clip insertion and deployment method will now be described in conjunction with FIGS. 14A-20. The instruments 160, 162 are slidably inserted thought the sheath channels 157a, 157b and advanced so their jaws extend distal of the hubs 156a and 156b and engage the clip 120. The hubs 156a, 156b are in their angled position as shown in FIG. 14A to angle the distal portion (and jaws) of the instrument into engagement with the clip 120. With instruments 160, 162 engaged with the clip 120 as shown in FIG. 14A, no force is applied to the clip 120 and no force is applied to the links 151a/151b and push-pull mechanism 152a/152b. This allows the hubs 156a, 156b to angle inwardly and the instrument jaws to be aligned with the clip 120 for grasping of the clip 120. To controllably open the clip, a pull force is applied to the hubs 156a, 156b via the elongated members 152a, 152b. By pulling the members 152a, 152b proximally, the hubs 156a, 156b via links 151a, 151b pivot radially outward away from the longitudinal axis, thereby moving the distal portions of the shafts 165, 167 of the flexible instruments 160, 162 radially outwardly to the straighter position of FIG. 14B. Such movement expands the clip 120 into the open position of FIG. 14B. Note in this embodiment, the shafts 165, 167 are in a linear position, however, in other embodiments, the shafts can be flexed to other angles in order to fully open the clip 120.

Figure 15:
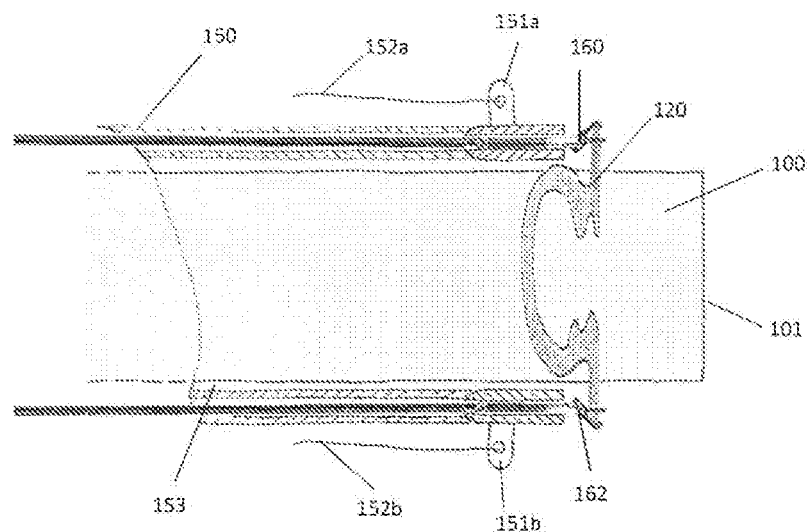
FIG. 15 is a side view similar to FIG. 14B showing advancement of the endoscope within the sheath.
Figure 16A:
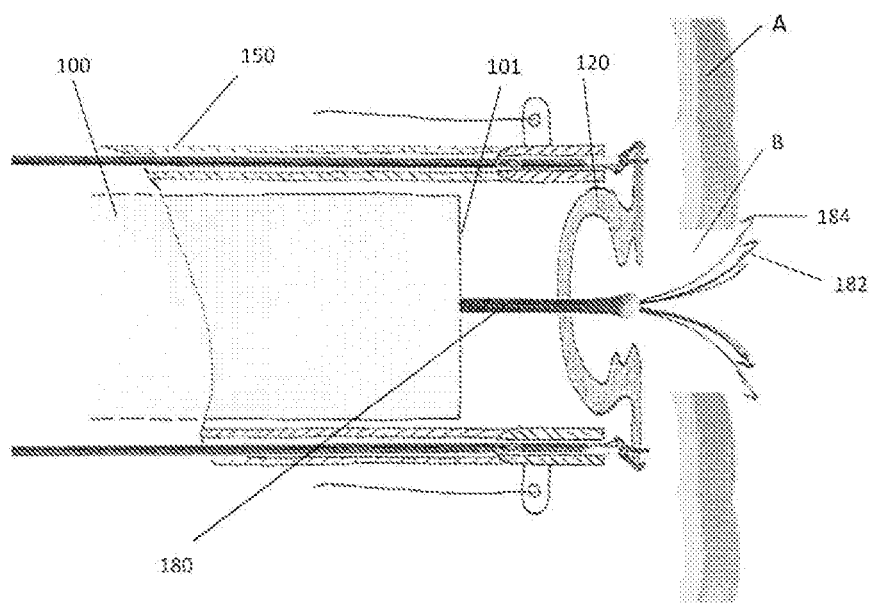
FIG. 16A is a side view similar to FIG. 15 showing retraction of the scope and advancement of a tissue retractor to approximate and retract the tissue into the open clip.

With the clip 120 in the open position, the flexible scope 100 is advanced through the scope channel 153 of the sheath 150 beyond the distal end of the sheath 150 to a position adjacent the target tissue site to visualize the target tissue (FIG. 15). In this position, the distal end 101 of the scope 100 is distal of the sheath 150 and open clip 120. Using the scope 100 as a guide, the sheath 150 is then advanced until the clip 120 is located in a close proximity to the target tissue A and the scope 100 is retracted proximally within the sheath 150. Note in this position the distal end of the sheath 150 (and clip 120) is distal of the distal end 101 of scope 100 as shown in FIG. 16A.

Figure 16B:
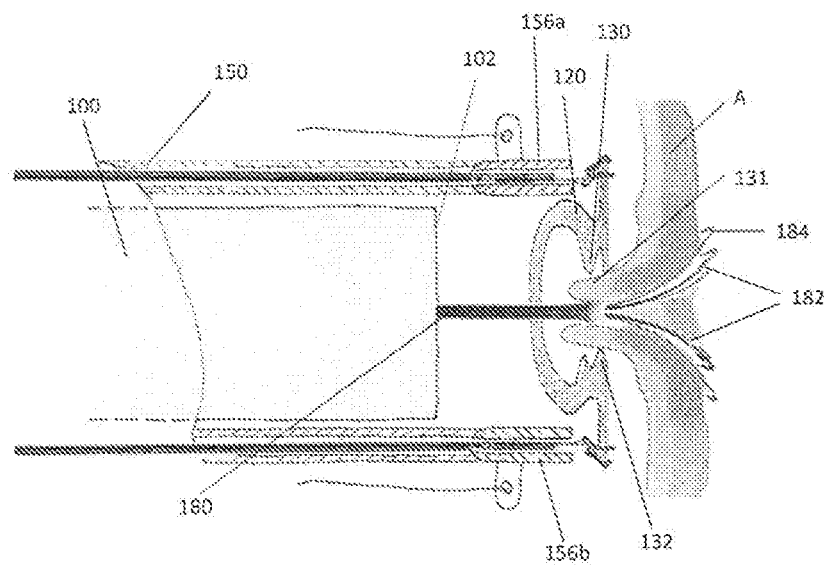
FIG. 16B is a side view similar to FIG. 16A showing the tissue approximated by the retractor.

Next, a tissue grasper 180 (FIG. 16A) having a plurality of tissue grasping arms 182 with penetrating members such as tines 184 is inserted through a working channel of the scope 100. The grasper 180 can have six arms, for example spaced 60 degrees apart, however, a different number of arms and/or a different spacing is also contemplated. The grasper 180 is advanced to grasp the tissue from the underside and the arms 182 are retracted to approximate the edges of the defect B. The arms 182 pull the tissue A into the clip tissue opening 134 as shown in FIG. 16B. The scope 100 remains in the retracted position so as not to interfere with the tissue. Note as an alternative to the grasper 180, a different grasper can be used or two or more graspers with grasping jaws or tissue engaging arms can be inserted through separate scope channels.

Figure 17:
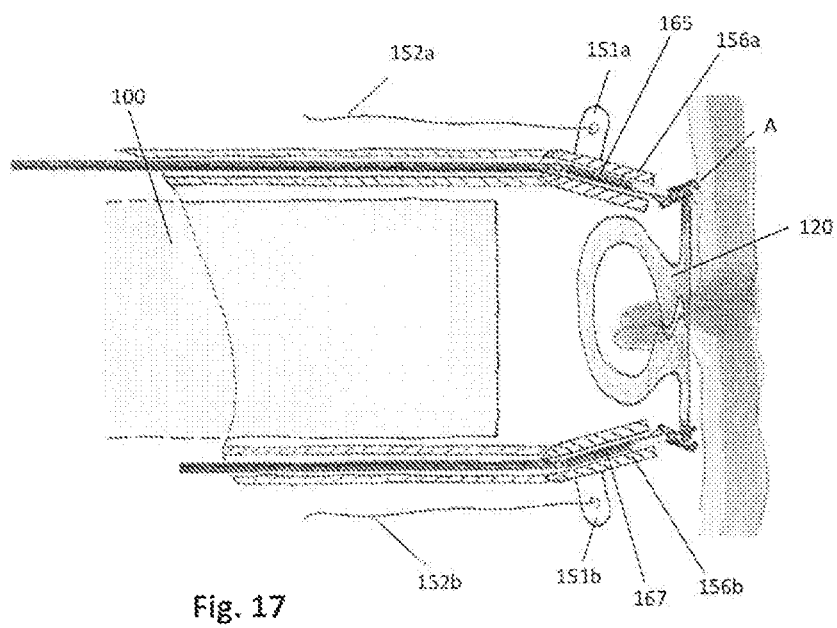
FIG. 17 is a side view similar to FIG. 16B showing release of the force on the links to allow the clip to return to the closed position to compress tissue.
Figure 18:
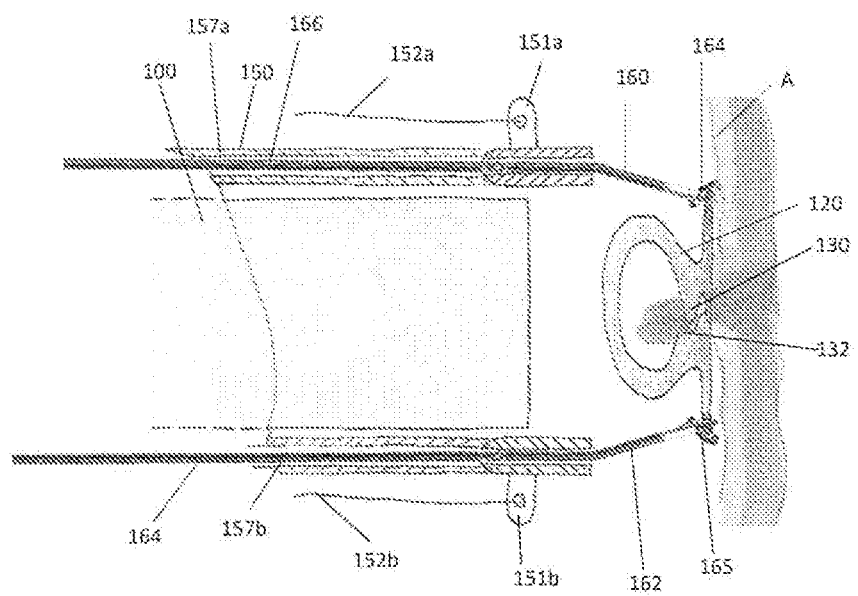
FIG. 18 is a side view similar to FIG. 17 showing the sheath retracted to increase the field of view.

The push-pull links 152a, 152b are then released so they no longer apply the proximal force to the hubs 156a, 156b, allowing the hubs 156a, 156b to return to their inwardly angled position, effecting bending of the shafts 165, 167 so the clip 120 can move back to the closed position to close and compress/clamp the tissue A between the tissue contacting (engaging) surfaces 131, 133 (FIG. 17). The push pull links 152a, 152b can be released for example by pivoting of proximal links 152c, 152e (connected to push-pull members 152a, 152b) about pivots 152d, 152f, respectively (FIG. 14C), although other mechanisms actable at a proximal end of the system for moving members 152a, 152b are also contemplated. Note the elongated members 152a, 152b can be moved slowly or incrementally to provide controlled closure of the clip 120 if desired. With the instruments 160, 162 still connected to the clip 120, the user can visually confirm through the scope 100 proper placement of the clip 120 over the tissue A. Moreover, with the instruments 160, 162 still connected to the clip 120, the sheath 150 can be retracted if desired as shown in FIG. 18 to further visually confirm through the scope 100 proper placement of the clip over the tissue A as such retraction increases the field of view. Note in preferred embodiments, retraction of the sheath 150 does not affect the clip position since the position of the flexible instruments 160, 162 does not change as the sheath channels 157a, 157b slide over the flexible instrument shafts 165, 167 and the jaws remain clamped on the closed clip 120 continuing to hold the clip 120. Since the instruments 160, 162 are still engaged with the clip 120, if the clip placement is not satisfactory, the deployment process could be repeated by reopening the clip 120, i.e., by applying a proximal pull force via members 152a, 152b to straighten the hubs 156a, 156b and following the steps above to place and close the clip 120. Once the position of the clip 120 is satisfactory to the clinician, the jaws 164, 169 of the instruments 160, 162 are open to release the clip 120 from the instruments 160, 162, and the instruments 160, 162, along with the sheath 150 and scope 100, are withdrawn from the patient's body leaving the clip 120 in the body.

Thus, as can be appreciated, the user can visually confirm that the clip captures tissue appropriately and circumferentially before the delivery device is disconnected leaving the clip in place. If necessary, the user can re-open and reposition the clip if its location is not satisfactory. If the delivery device is disconnected from the clip, the user can re-connect to it and reposition as necessary.

Also, as can be appreciated, the clip is configured to allow an engagement with the clip actuating mechanism of the delivery system. There could be a multiple connection points. The mechanism connects to these multiple connection points and can deliver the opening force independently to each such point in some embodiments. After the clip is delivered and its proper placement is confirmed, the delivery device is disconnected from the clip. The force could be applied to just one side of the clip, while the other side is held stationary. Alternatively, the force could be applied to all connection points simultaneously or to one point at a time.

To assure optimal closure in certain applications, the clip can be positioned such that the target tissue is captured evenly. To achieve this, the tissue can be retracted within the clip preferably equidistantly to the teeth that are located on the compression surfaces of the clip and to equal depth circumferentially relative to the teeth. In certain alternate applications, the tissue could be asymmetrically captured.

Figure 19:
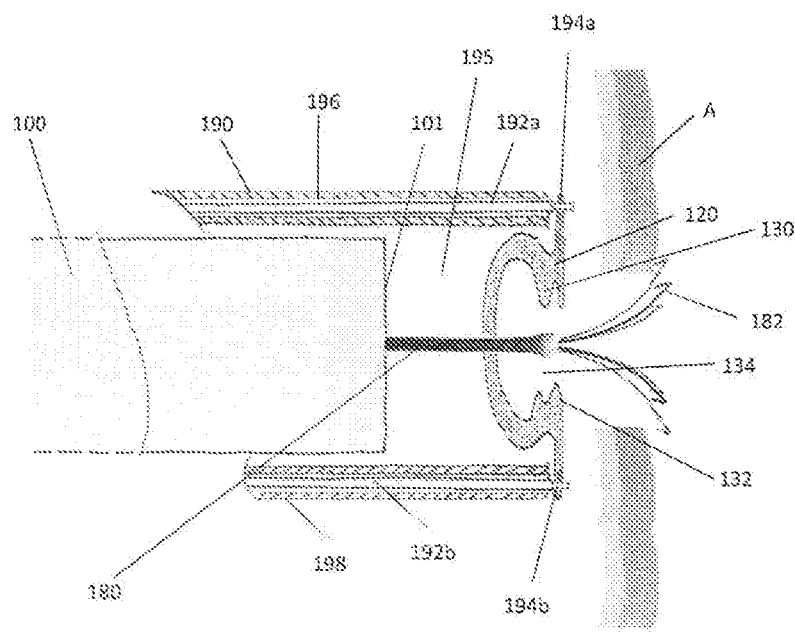
FIG. 19 is a side view of an alternate embodiment of the clip deployment system having retractable pins engageable with the clip, the sheath shown in cross-section.
Figure 20:
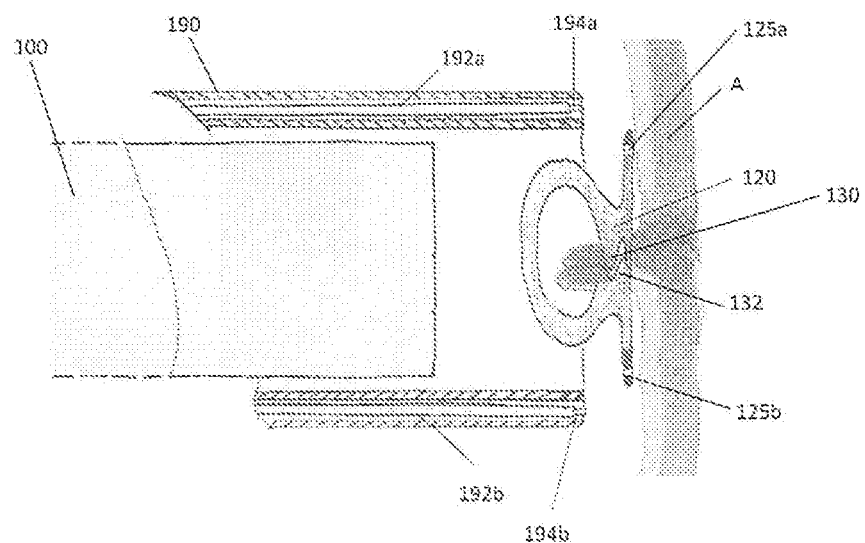
FIG. 20 is a side view similar to FIG. 19 showing the pins retracted into the sheath to release the clip so the clip returns to its closed condition.

FIGS. 19 and 20 show an alternate embodiment of the clip deployment system for engaging and releasing the clip 120. In this embodiment, instead of the pivoting hubs 156a, 156b, sheath 190 includes an elongated member 192a having a retractable pin 194a at its distal end and an elongated member 192b having a retractable pin 194b at its distal end. In this embodiment, the delivery system holds the clip in the open position until the tissue is introduced into it. Then, the delivery mechanism is simply disengaged from the clip allowing it to spring into its closed position and clamp tissue.

Elongated members 192a, 192b can be in the form of a rod or tube and slide within channels 196, 198, respectively of sheath 190. The pins 194a, 194b extend through openings 125a, 125b (e.g., the same openings that receive the jaws in the embodiment of FIG. 14A) of the pre-loaded clip 120 and are shown in FIG. 19 engaged with the openings to force the clip 120 to the open position. Thus, in this extended (advanced) position, they apply a force to opposing sides of clip 120 to radially expand (spread) the clip 120 to the open position. To close the clip 120, the pins 194a, 194b are retracted, i.e., pulled proximally by proximal retraction of elongated members 192a, 192b, to the position of FIG. 20, thereby disengaging from the openings 125a, 125b of clip 120 to release the clip 120, allowing it to return, e.g., spring back, to its normally closed position. Note in this embodiment, like in the embodiment of FIGS. 14A-18, the scope 100 can if desired be initially advanced through the open clip 120 to view the target issue, and then retracted so its distal end 101 is proximal of the distal end of the sheath 190. Retractor 180 (or other tissue retractors) as described above can be advanced for example through the scope channel of scope 100 to pull tissue into the opening 134 in the clip 120 so the release of the clip 120 applies a compressive force to tissue via the engagement of the clip's opposing tissue contacting surfaces.

In the alternate embodiment of FIGS. 43-46B, the clip engagement member is inserted through a working channel of the endoscope rather than through a channel of the sheath. More specifically, clip engagement member 300 has a shaft 301 and a pair of jaws 302, 304 pivotable about hinge 306. The clip jaws 302, 304 engage openings 98a, 98b of clip 80. Note clip 80 of FIG. 6A is shown by way of example as other clips disclosed herein can also be engaged/manipulated by clip engagement 300 extending through the scope channel. The jaws 302, 304 are opened to move the clip 80 from the closed position of FIG. 43 to the open position of FIG. 44 to spread (radially expand) the clip 90 from the closed position to the open position for clip opening 81 to receive tissue. Note the jaws 302, 304 can be articulated about pivot 308 in the embodiment of FIG. 45 to change the orientation of clip 80. In this embodiment of FIG. 45, the shaft 301 is inserted through scope channel 105 but alternatively could be inserted through scope channel 103 of FIG. 43. Tissue graspers 310, 320 are inserted through sheath channel 330, 334 of the sheath which is placed over the endoscope. Tissue grasper 310 has jaws 312, 314 which pivot about pivot 316 to move between the open and closed positions to grasp tissue. Tissue grasper 320 has jaws 322, 324 which pivot about pivot 326 to move between the open and closed positions to grasp tissue. One of both of the jaws 312, 314 and one or both of the jaws 322, 324 can pivot. The instrument jaws are pivoted by actuation at proximal end 318, 328, e.g., by pulling or pushing the looped handle. Note the instrument 310 is inserted through the proximal end 331 of sheath channel 330 and exits at the distal end 335 of sheath channel 330. Note the instrument 320 is inserted through the proximal end 333 of sheath channel 334 and exits at the distal end 337 of sheath channel 334. The clip engaging/manipulating member is inserted though port 307 of scope 100, and extends through scope channel 103, and is manipulated at proximal end 307 which pulls jaw actuating wire or shaft 309. Other clip engagement members could alternatively be inserted through the scope working channel.

Figure 50:
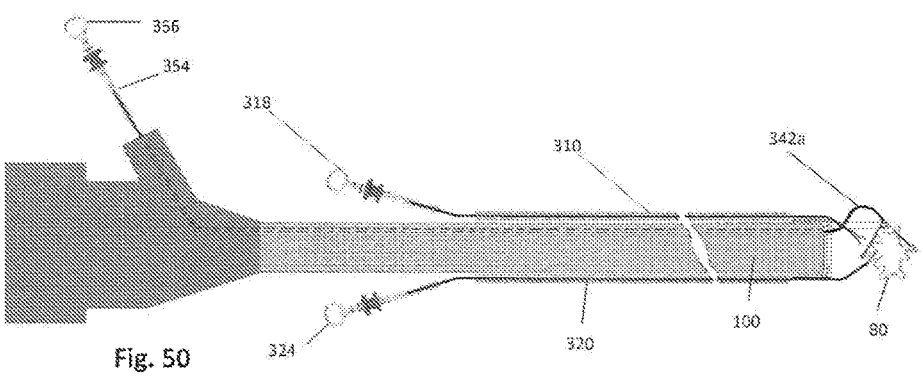
Figure 51:
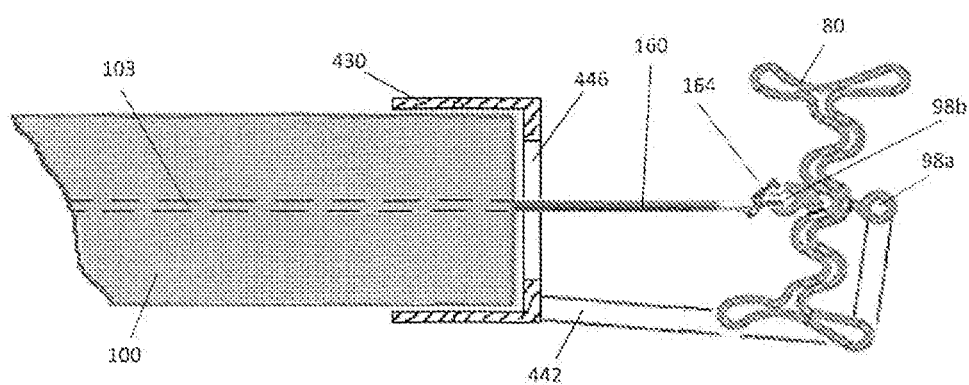
FIGS. 51-54 are side views of an alternate embodiment of a delivery system of the present invention, the clip shown in the closed and delivery position in FIG. 54, in the closed position for placement in FIG. 51 and in the open position in FIGS. 52 and 53.

In the alternate embodiment of FIGS. 47-50, cap 330 has a distally extending post 342 and is mounted over a distal end of the endoscope 100. Cap 330 can include an aperture 346 for the endoscope. Clip engaging member (instrument) 350 has jaws 352, 354 which are rotationally attached to the post 342 at pivot 344. The jaws 352, 354 are manipulated to open and close the clip 80 via engagement with clip openings 98a, 98b. The clip engaging member 350 is backloaded through the endoscope channel 109 and then a handle 356 is attached to the proximal end of the instrument 350. By pushing on the instrument, the shaft 342 buckles at region 342a (due to the fixed connection to the post) to rotate the jaws 352, 354 relative to the longitudinal axis of the scope 100. FIG. 50 illustrates tissue graspers 310, 312, with proximal handles 318, 324, inserted through the channels of sheath 320 by way of example. Other tissue graspers could alternatively be inserted.

Figure 52:
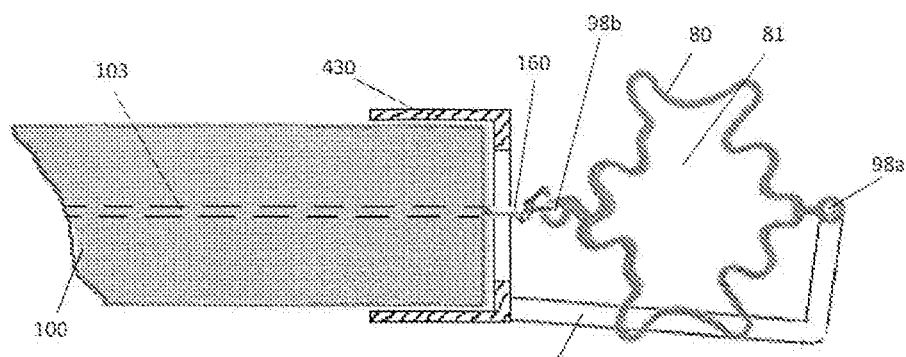
Figure 53:
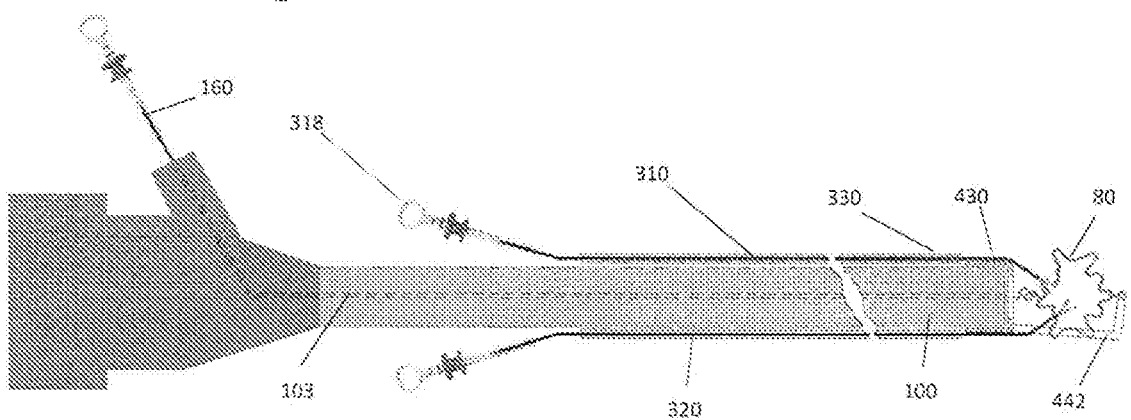
Figure 54:
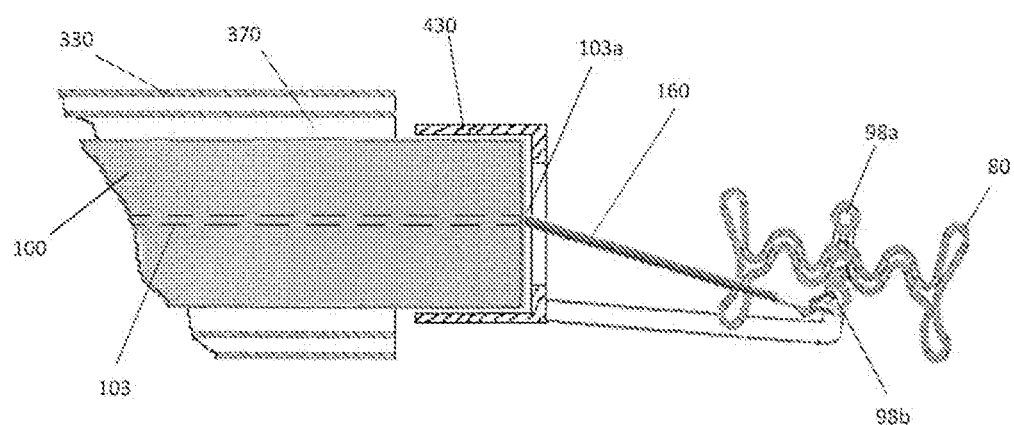

In the embodiment of FIGS. 51-54, cap 430 is mounted over a distal end of the endoscope 100. Cap 430 can include an aperture 446 for the endoscope. A post 442 extends from cap 430 and is L-shaped with a first portion extending longitudinally from the cap 430 and a second portion transverse to the first portion and extending transverse to a longitudinal axis of the scope 100. Clip engagement member 160 has a shaft and a pair of jaws 164 pivotable about a hinge as in instrument 160 described above. The clip jaw 164 engages opening 98b of clip 80. Note clip 80 of FIG. 6A is shown by way of example as other clips disclosed herein can also be engaged/manipulated by clip engagement member 160 extending through the scope channel. The end of the post 442 engages opening 98a of clip 80. In the insertion position of FIG. 54, the shaft of instrument 160 is pivoted (articulated) to reorient the clip to a longitudinal position. This reduces the profile for insertion since the length of the clip exceeds the diameter of the endoscope 100. After insertion, the instrument 160 returns to its straight position to rotate the clip 80 to the position of FIG. 51. To open the clip, instrument 160 is retracted which radially expands the clip as shown in FIG. 52. Thus, the clip opens longitudinally. In this embodiment of FIG. 51, the shaft is inserted through scope channel 103 but alternatively could be inserted through scope channel 105 such as in FIG. 45. Tissue graspers 310, 320, as shown in FIG. 53, are inserted through sheath channel 330, 334 of the sheath which is placed over the endoscope 100 and are manipulated to retract tissue in the same manner as described above in the embodiment of FIGS. 46A and 46B. Note one of both of the jaws can pivot. The instrument jaws are pivoted by actuation at proximal end 318, 328, e.g., by pulling or pushing the looped handle as described above. Note other clip engagement members could alternatively be inserted through the scope working channel. Note also other tissue graspers can be utilized.

Figure 55:
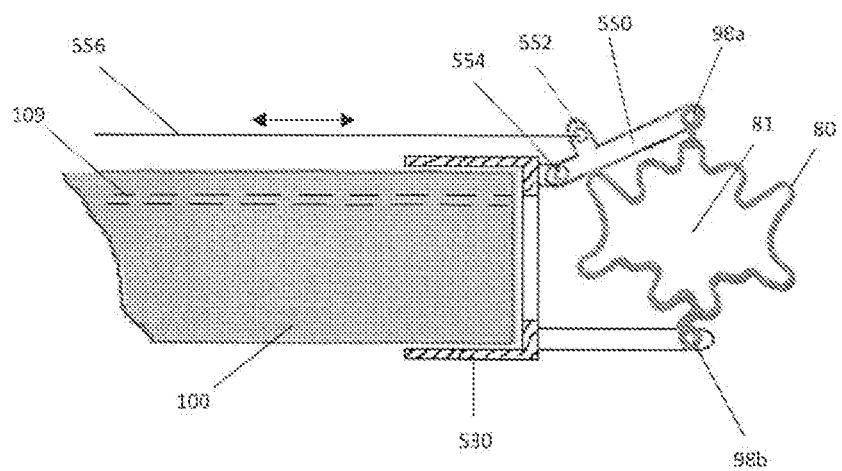
FIG. 55 is a side view of an alternate embodiment of a delivery system of the present invention, the clip shown in the open position.

In the alternate embodiment of FIG. 55, the clip 80 opens across rather than longitudinally as in FIG. 52. Cap 530 has a first post that engages opening 98b of clip 80 and a second pivotable post 550 which engages opening 98a of clip 80. To open the clip to the position of FIG. 55, actuator, e.g., wire or rod, 554, attached at pivot 552 to link 550, is pulled to pivot the link upwardly, e.g., away from the longitudinal axis of the scope 100, to spread the clip 80 radially to open the clip. Thus, the clip opens away from the longitudinal axis rather than along the axis as in FIG. 52. Note sheath 530 has an opening for the endoscope 100. Clip 80 is shown by way of example; other clips disclosed herein could be used with the clip deployment mechanism of FIG. 53.

FIGS. 1-20 discussed above are directed to a clip which is radially expandable by spreading the two sides of the clip apart. FIGS. 21-39 illustrate alternate embodiments wherein the clip has hinged sections so the clip sides are pivoted with respect to each other. Thus, with the clips of FIGS. 1-20, the tissue contacting surfaces on the first and second sides of the clip face each other in the closed position of the clip and face or substantially face each other in the open position. In contrast, in the clips of FIGS. 21-39, the tissue contacting surfaces face each other in the closed position but are pivoted away so they do not face each other in the open position of the clip.

Figure 21:
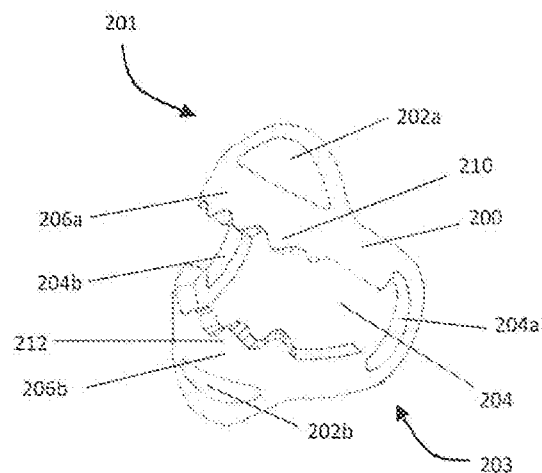
FIG. 21 is a perspective view of a first embodiment of the hinged clip of the present invention shown in the open position.

Turning first to the embodiment of FIG. 21, clip 200 has a first side 201 with a tissue contacting surface 210 having a plurality of teeth 206a. Second side 203 of clip 200 has a tissue contacting surface 212 with teeth 206b. Clip 200 is shown in the partially open position in FIG. 21. The two sides 201, 203 pivot about (around) hinged areas 204a 204b. The first side 210 has an opening 202a and the second side has an opening 204a forming receiving portions to receive the clip engagement members for manipulating the clip, i.e., for opening the clip, as described below.

Clip 230 of the embodiment of FIG. 23B is similar to clip 200 except for the concavity in the hinged area 232 (and the concavity in the other hinged area not shown). Thus, clip 230 has a first side with a tissue contacting surface 233 having a plurality of teeth 234 and a second side having a tissue contacting surface 235 with a plurality of teeth 236. The concave area in hinged area 232 receives projecting hub or hinge support 220 of sheath 214 of the clip insertion and deployment system. Note the hinged areas 204a, 204b of clip 200 are convex so they would mate with a hub (hinge support) having a concave or inwardly curved region. In either case, the hinged areas of the clip engage the hinge support of the sheath so the hub provides a support to hold the clip as the sides of the clip are pivoted to an open position.

The sheath 214 has an opening or lumen (channel) 218 to receive a flexible endoscope, colonoscope, laparoscope, etc. as the hollow sheath 214 is configured and dimensioned to be positioned over an endoscope, e.g., frictionally fit over the scope. Thus, the sheath 214 includes a scope channel 218, preferably a center channel, and separate channels, radially spaced from the scope channel 218, for the actuators (manipulators) for controlling the clip 230. The sheath 214, as well as the other sheaths disclosed herein as alternate embodiments, can be positioned only over a distal region of the endoscope, over a more substantial region of the endoscope or over the entire endoscope. That is the sheath can be in the form of a hollow sleeve placed over the entire scope or formed as an attachment to the distal end of the scopes or only a portion of the scope.

The deployment system includes a first clip engagement member 227 in the form of a hook and a second clip engagement member 229 also in the form of a hook. The hooks 227, 229 extend through openings 232a, 232b of clip 230 (which can be similar to openings 202a, 202b of FIG. 21) to retain the clip 230 on the sheath 214. Elongated slidable member 224, e.g., a rod or tubular member (tube), slides within channel 216a of the sheath 214 and slidable member 226, e.g., rod or tubular member (tube), slides within channel 216b of sheath 214. As in the other embodiments disclosed herein, the elongated members can be part of the sheath (e.g., connected) to the sheath or separate components insertable into the sheath. Hook 227 is connected to elongated member 224 and hook 229 is connected to elongated member 226 so that movement of the members 224, 226 effects movement of the respective hook 227, 229. The elongated members 224, 226 are actuated by the clinician outside the patient's body via a control mechanism such as for example the mechanism shown in FIG. 14C. Note the channels for the elongated members 224, 226 can be formed in a wall of the sheath 214 as shown, or alternatively, can be a separate channel formed outside of the outer wall of the sheath. The elongated members 224, 226 are shown in the extended position in FIG. 23, and can slide within the channels 216a, 216b of the sheath 214. When retracted, the elongated members 224, 226 move the hooks proximally to apply a force to opposing sides of clip 230 to force the clip 230 to pivot to its open position. Note the elongated members with hooks are one example of clip engaging members to manipulate the clip, it being understood that alternate clip engaging members can be utilized to perform the function of manipulating, e.g., opening, the hinged clip as described herein.

Figure 23C:
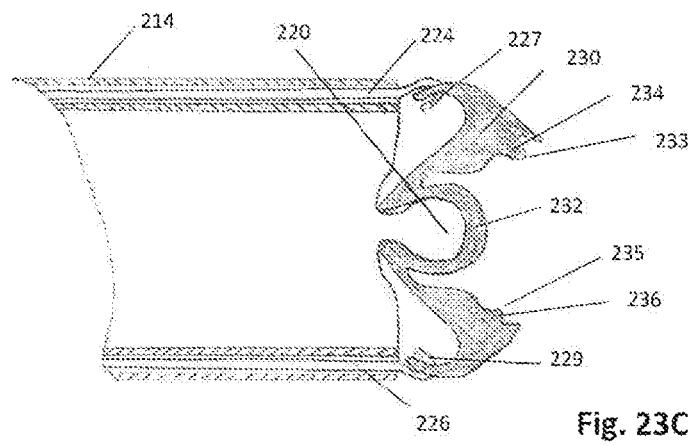
FIG. 23C is a view similar to FIG. 23B showing the links retracted to pivot the surgical clip to an open position to receive tissue.

Turning now to the insertion and deployment method for applying clip 230 and with reference to FIGS. 23B-28, in the initial position, the elongated members, e.g., links, 224 and 226, and thus the connected hooks 227, 229 are in the extended position with the preloaded clip in the closed position as shown in FIG. 23B. In this closed position, the teeth 234, 236 can partially or alternatively fully intermesh. With hooks 227, 229 engaged with the clip 230 as shown in FIGS. 23B and 26A, no force is applied to the clip 230 as no force is applied to the elongated members 224, 226. To controllably open the clip, a pull force is applied to the hooks 227, 229 via the elongated members 224, 226 by pulling the elongated members 224, 226 proximally, e.g., by a proximal actuator(s). This causes the two opposing sides of the clip to be pivoted away from each other about hinges 232 as the hinged regions 232 are held stationary by the hub 220 as they rest against the hub (hinge support) 220 and a force is applied to the clip sides as shown in FIGS. 23C and 26B. Note as the clip is opened, the tissue contacting surfaces 233, 235 (and their respective teeth 234, 236) are pivoted away from each other, deforming the hinge 232, to open a space for receipt of tissue.

Figure 26A:
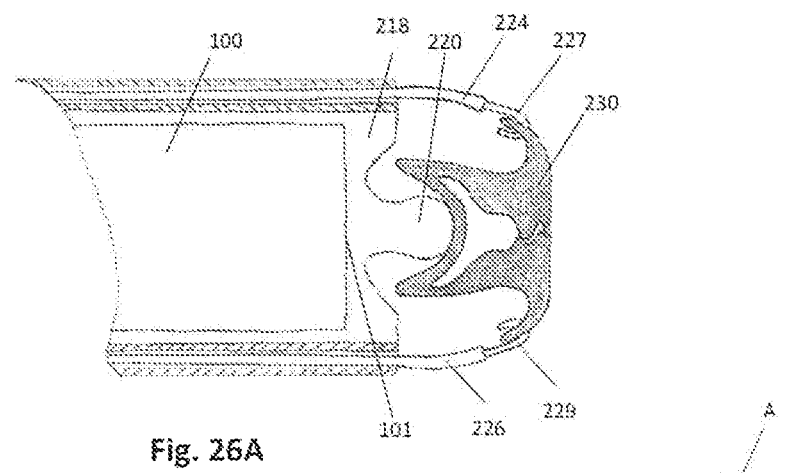
FIG. 26A is a side view similar to FIG. 23B showing an endoscope within the sheath.
Figure 26B:
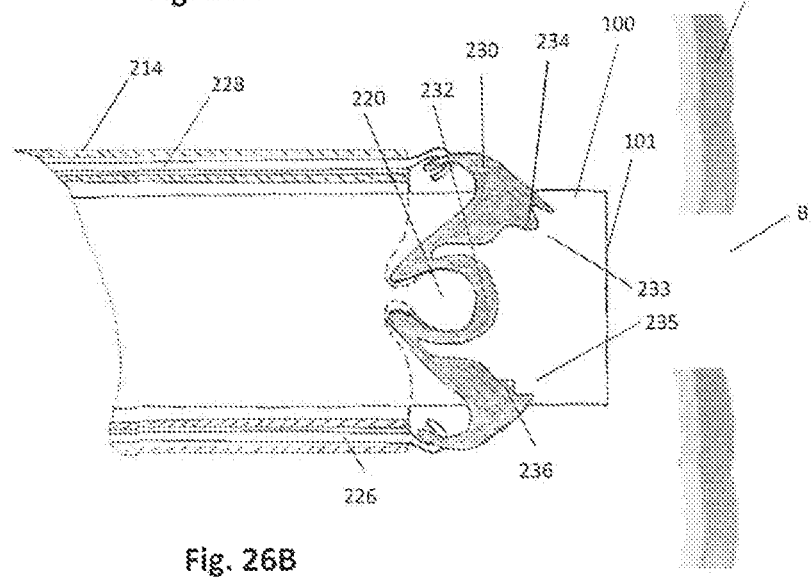
FIG. 26B is a side view similar to FIG. 26A showing a force applied to the links to expand the clip into the open condition (position) for receiving tissue and the endoscope advanced from the sheath.
Figure 26C:
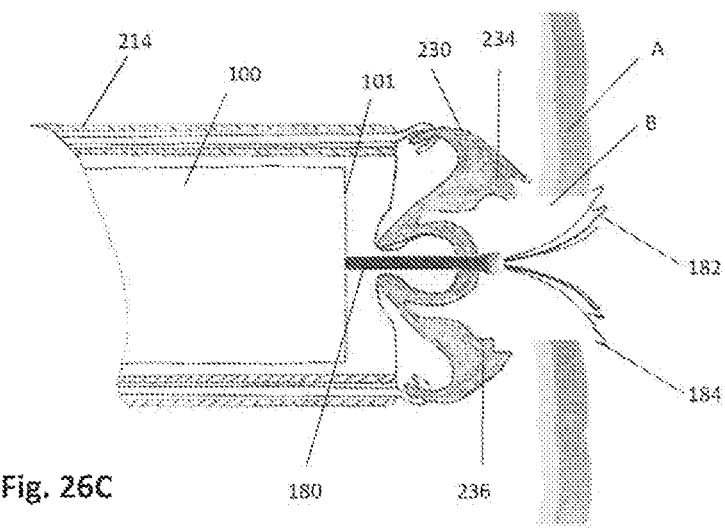
FIG. 26C is a side view similar to FIG. 26B showing retraction of the endoscope and advancement of a tissue retractor to approximate and retract the tissue into the open clip.

With the clip 230 in the open position, the flexible scope 100 is advanced through the sheath channel 218 of the sheath 214 beyond the distal end of the sheath 214 and through the open clip 230 to a position adjacent the target tissue site to visualize the target tissue (FIG. 26B). In this position, the distal end 101 of the scope 100 is distal of the sheath 214 and the open clip 230. Using the scope 100 as a guide, the sheath 214 is then advanced until the clip 230 is located in close proximity to the target tissue A and the scope 100 is retracted proximally within the sheath 214. Note in this position the distal end of the sheath 214 (and clip 230) is distal of the distal end 101 of scope 100 as shown in FIG. 26C.

Next, a tissue grasper 180 (FIG. 26C), which can be the same tissue grasper as shown in FIG. 16A having a plurality of tissue grasping arms 182 with penetrating members such as tines 184, or another tissue grasper(s), is inserted through a working channel of the scope 100. The grasper 180 grasps the tissue from the underside and the arms 182 are retracted to approximate the edges of the defect B as described above. The arms 182 pull the tissue A into the clip tissue opening. The scope 100 remains in the retracted position so as not to interfere with the tissue.

Figure 26D:
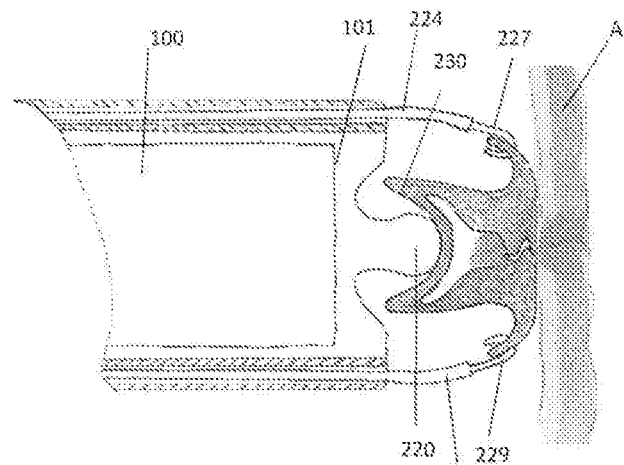
FIG. 26D is a side view similar to FIG. 26C showing the tissue approximated by the retractor and the clip in the closed position compressing tissue.
Figure 27:
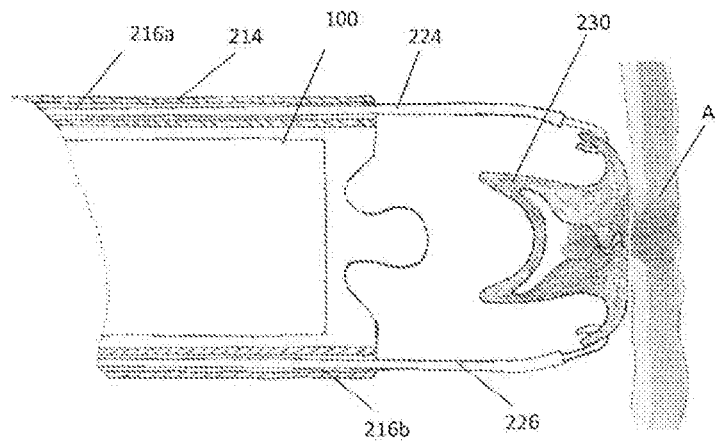
FIG. 27 is a view similar to FIG. 26D showing the sheath retracted to increase the field of view.
Figure 28:
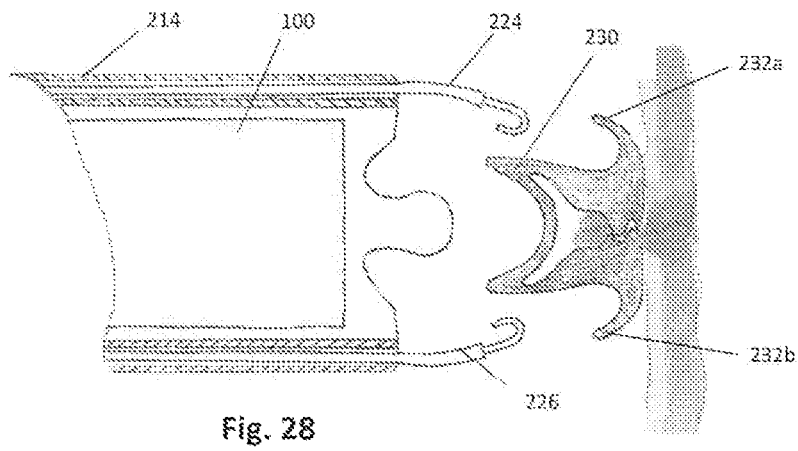
FIG. 28 is a view similar to FIG. 27 showing the disconnection of the links and removal of the sheath and endoscope, leaving the clip closed on tissue.

The elongated members 224 and 226 are then advanced so the hooks 227, 229 no longer apply the proximal force to the clip 230, allowing the clip 230 to move back to the closed position to close and compress/clamp the tissue A between the tissue contacting (engaging) surfaces 233, 235 (FIG. 26D). Note the elongated members 224, 226 can be moved slowly or incrementally to provide controlled closure of the clip 230 if desired. With the hooks 227, 229 still connected to the clip 230, the user can visually confirm through the scope 100 proper placement of the clip 230 over the tissue A. Moreover, with the hooks 227, 229 still connected to the clip 230, the sheath 214 can be retracted if desired as shown in FIG. 27 to further visually confirm through the scope 100 proper placement of the clip 230 over the tissue A as such retraction increases the field of view. Note preferably retraction of the sheath 214 does not affect the clip position since the position of the elongated members 224, 226 (and hooks 227, 229) does not change as the sheath channels 216a, 216b slide over the elongated members 224, 226. Since the instruments hooks 227, 229 are still engaged with the clip 230, if the clip placement is not satisfactory, the deployment process could be repeated by reopening the clip 230, i.e., by applying a proximal force via members 224, 226 and following the steps above to place and close the clip 230. Once the position of the clip 230 is satisfactory to the clinician, the hooks 227, 229 are removed from the openings 232a, 232b of the clip 230 (the elongated members 224, 226 can be advanced with respect to the sheath 214 to separate the clip 230 from the sheath 214) and the sheath 214 and scope 100 are withdrawn from the patient's body leaving the clip 230 in the body as shown in FIG. 28.

Thus, as can be appreciated, the user can visually confirm that the clip captures tissue appropriately and circumferentially before the delivery device is disconnected leaving the clip in place. If necessary, the user can re-open and reposition the clip if its location is not satisfactory. If the delivery device is disconnected from the clip, the user can re-connect to it and reposition as necessary.

Figure 24:
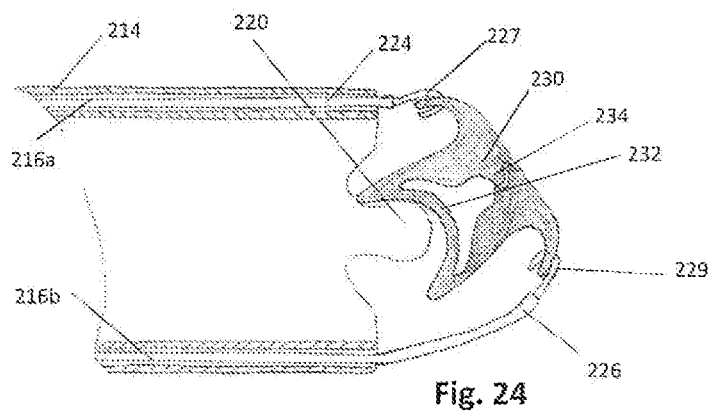
FIG. 24 shows one of the two links advanced to change the orientation of the clip relative to the sheath.
Figure 25:
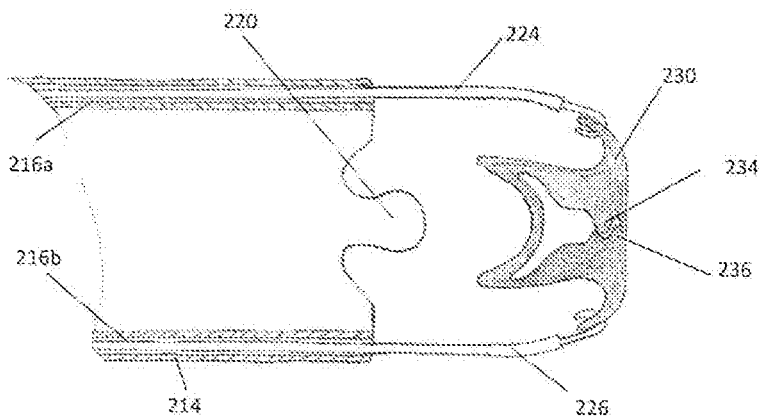
FIG. 25 shows both links advanced to separate the surgical clip from the sheath.

Preferably, the clip is oriented such that the target tissue is captured evenly. To achieve this, the tissue can be retracted within the clip preferably equidistantly to the teeth that are located on both sides of the clip and to an equal depth circumferentially relative to the teeth. In some instances, it might be difficult to achieve this in tight spaces, especially with devices which rely on the articulation of an endoscope for the clip positioning. Thus, these devices might have difficulty positioning the clip normally to the surface of the target tissue in tight spaces. The clip deployment system of FIG. 23A provides one example of enabling reorienting of the clip in tight spaces that might not otherwise be achievable by articulation of the scopes. FIG. 24 shows how this can be achieved. By asymmetrical actuation of the elongated members 224, 226, i.e., one elongated member being advanced (or alternatively pulled further than the other), the deployment system can change the orientation of the clip 230 relative to the longitudinal axis of the sheath. More specifically, in FIG. 24, as elongated member 226 is advanced, and the other side of the clip is held stationary or just slightly moved distally as elongated member 224 is held stationary or slightly moved distally. With this action, the clip 230 pivots in its closed position toward the side of the sheath containing sheath channel 216a and elongated member 224. This reorients the clip 230 so the clip is facing tissue at an angle to the longitudinal axis of the sheath rather than facing tissue distally as in FIG. 23B. As can be appreciated, to orient the clip 230 in the opposing direction (toward the side of the sheath containing sheath channel 216b and elongated member 226), elongated member 224 is advanced further, and the other side of the clip 230 is held stationary or just slightly moved distally as elongated member 226 is held stationary or slightly moved distally. Other mechanisms disclosed herein can also be used to reorient the clip. Also other clips disclosed herein can be reoriented in the same manner.

Figure 29A:
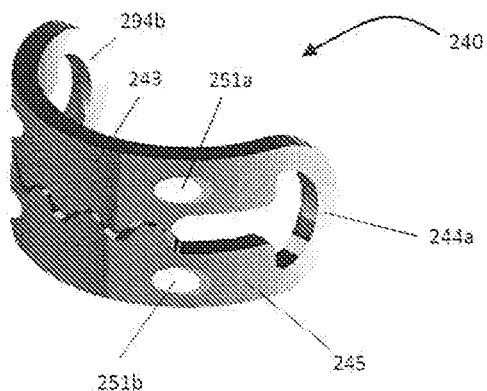
FIG. 29A is a perspective view of an alternate embodiment of the clip of the present invention shown in its normally closed condition (state)
Figure 29B:
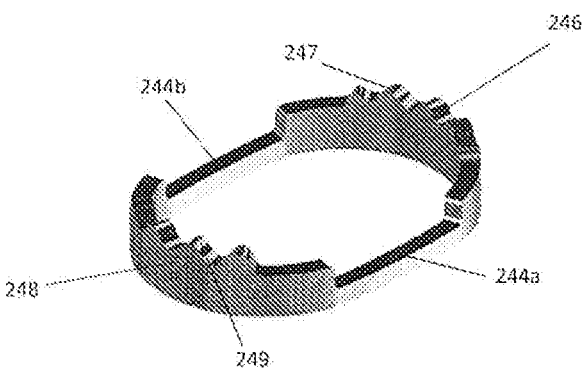
FIG. 29B is a perspective view of the clip of FIG. 29A shown in the fully open condition.
Figure 30:
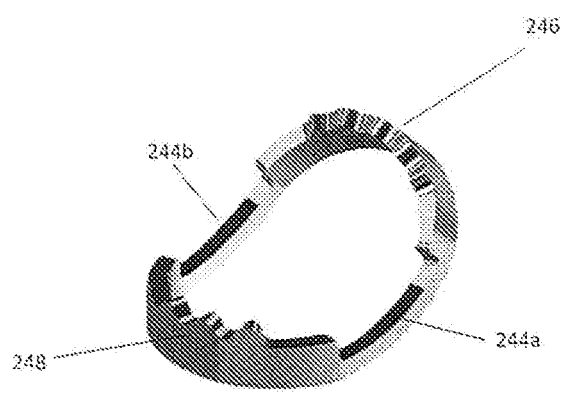
FIG. 30 is a perspective view of the clip of FIG. 29A shown in the mostly (semi) open condition.
Figure 31:
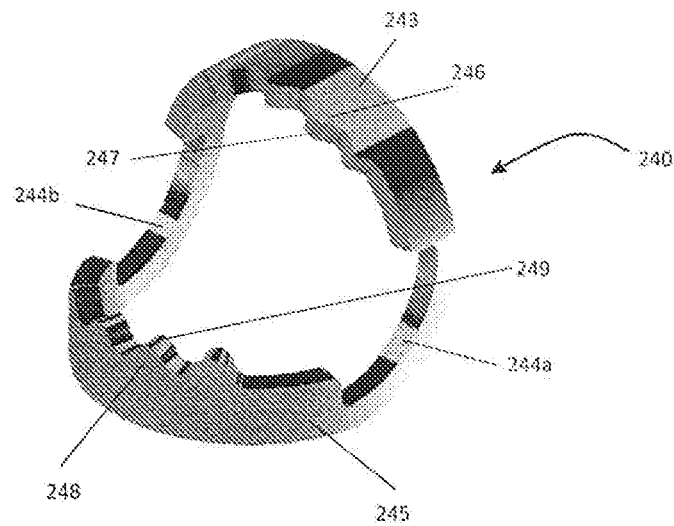
FIG. 31 is a perspective view of the clip of FIG. 29A shown in the half-closed condition.
Figure 32:
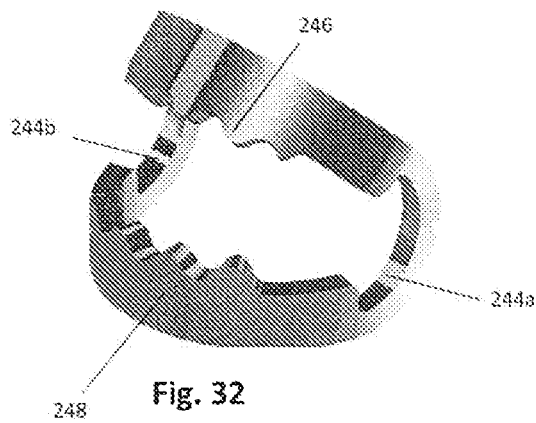
FIG. 32 is a perspective view of the clip of FIG. 29A shown in a ¾ closed condition.
Figure 33:
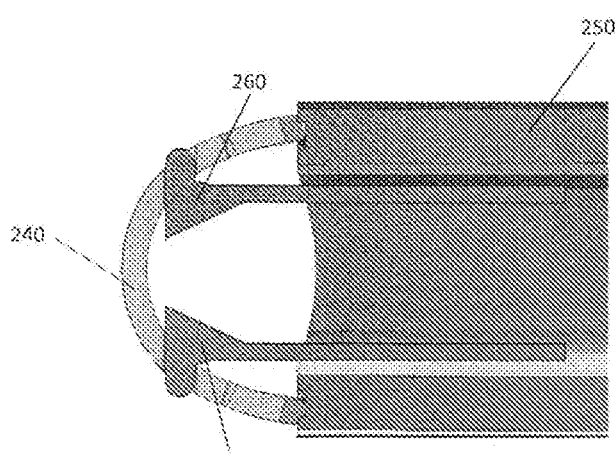
FIG. 33 is a side view of the embodiment of the delivery system showing the links engaging the clip of FIG. 29A.
Figure 42:
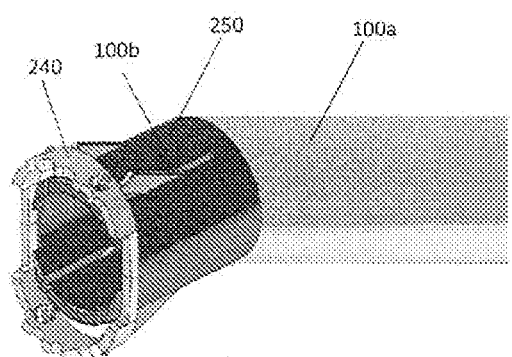
FIG. 42 is a perspective view illustrating articulation of the scope to change the orientation of the clip.
Figure 43:
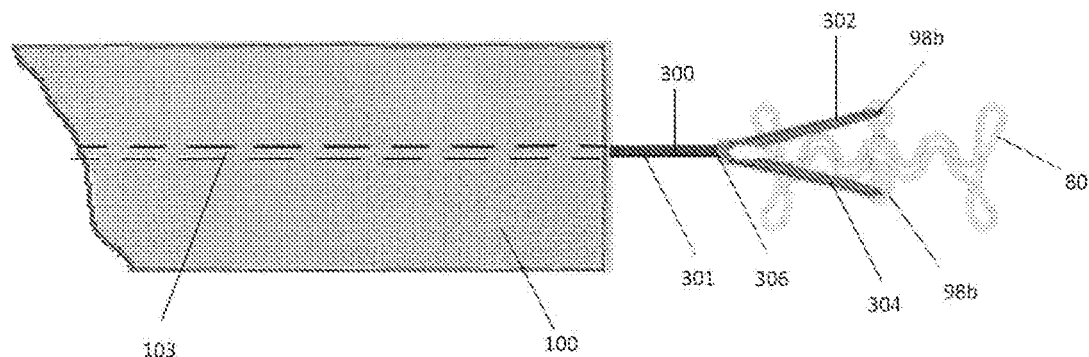
FIGS. 43 and 44 are side views of an alternate embodiment for opening the clip, the clip shown in the closed position in FIG. 43 and in the open position in FIG. 44.
Figure 44:
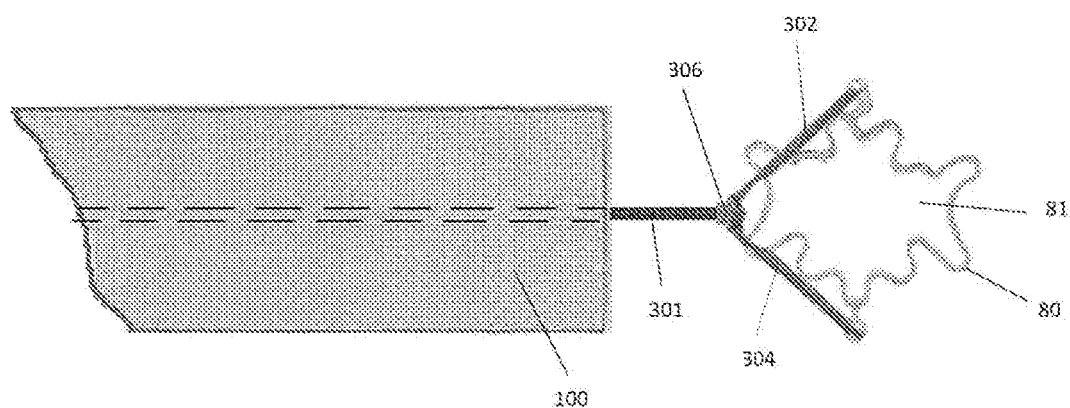
Figure 45:
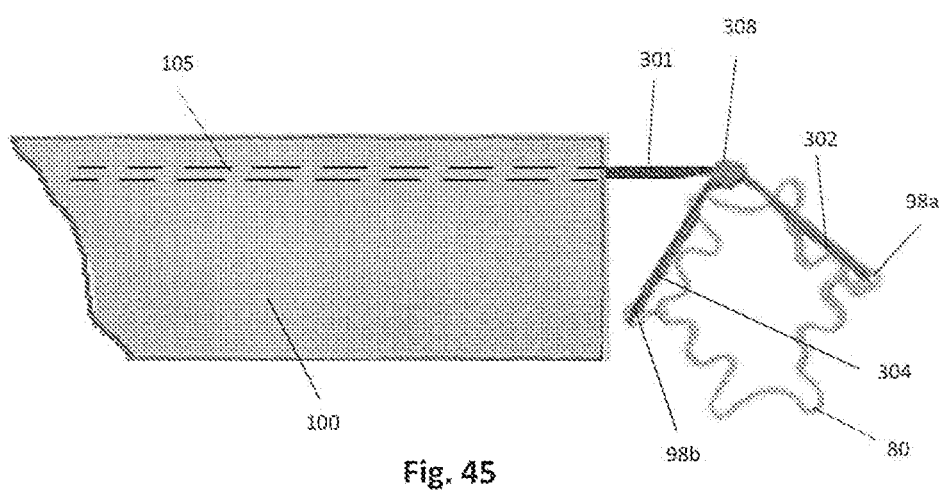
FIG. 45 is a side view similar to FIG. 43 showing articulation of the clip manipulator to change the orientation of the clip.
Figure 46B:
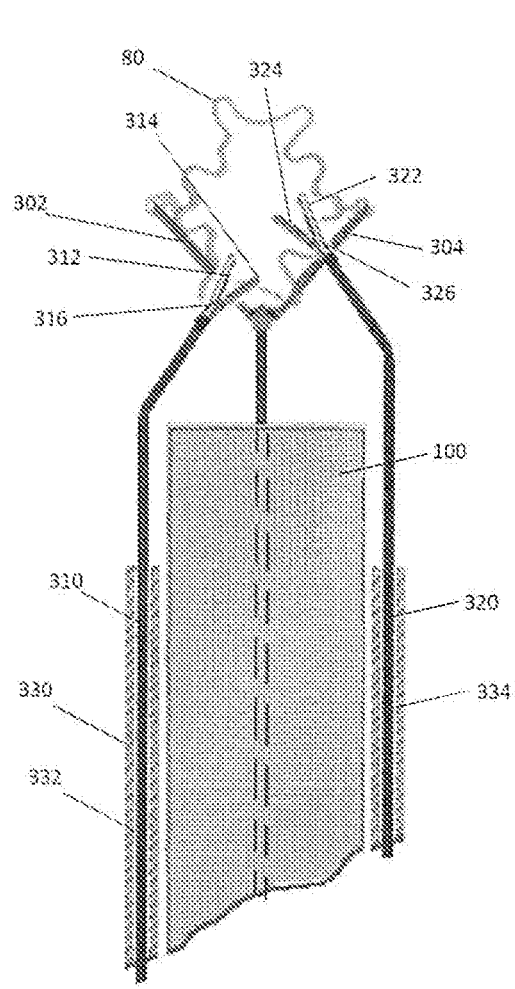
FIG. 46B is a close up of the area of detail identified in FIG. 46A.
Figure 46A:
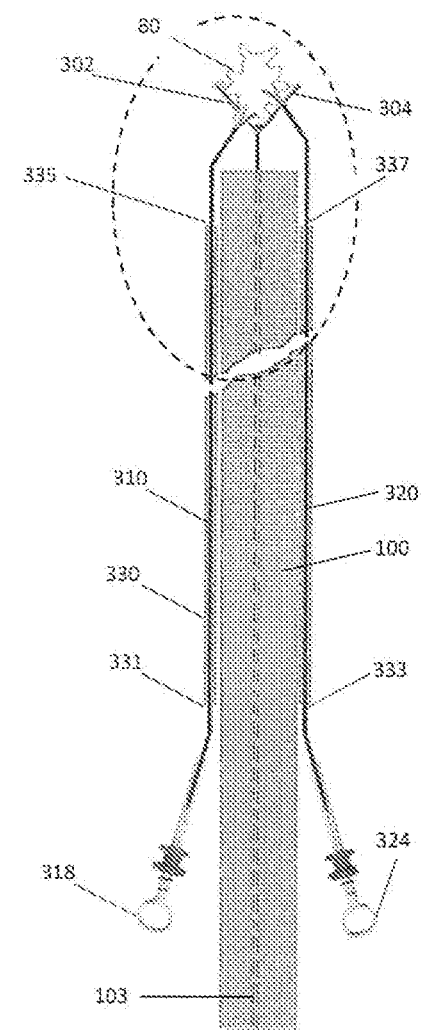
FIG. 46A is a side view showing the clip deployment system of FIG. 44 and tissue graspers inserted through the sheath.
Figure 47:
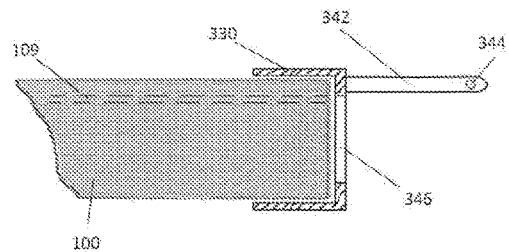
FIGS. 47-50 are side views of an alternate embodiment of a delivery system of the present invention, the clip shown in the closed position in FIG. 48 and in the open position in FIGS. 49 and 50.
Figure 48:
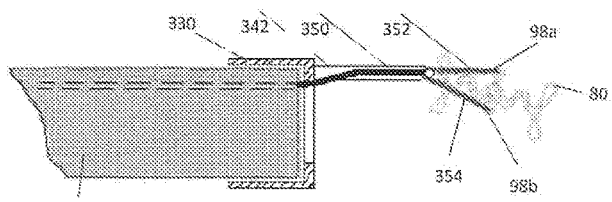
Figure 49:
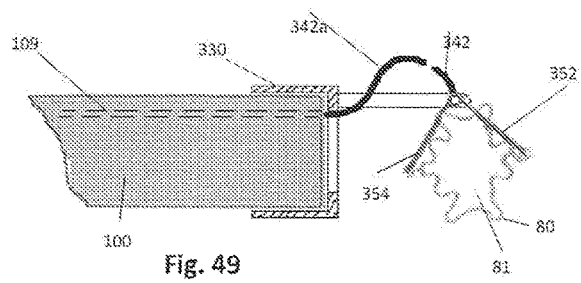

Note FIG. 42 illustrates an embodiment where, for example, the endoscope is utilized to change the orientation of the clip which could be implemented in certain applications. Scope 100a located within the sheath 250 is an articulating scope so the distal portion 100b can be angled relative to the longitudinal axis of the scope which articulates the distal end of the sheath 250 and changes the orientation of the clip. The scope is shown by way of example for changing the orientation of clip 240 of FIG. 29A discussed below, but can also be utilized to orient the other clips described herein. Sheath 250 of FIG. 33, which is used with clip 240, is also shown in FIG. 29A by way of example, although other sheaths and other clip engaging members/manipulators can be utilized with the articulating scope.

An alternate embodiment of the hinged pivoting clip is illustrated in FIGS. 29A-39. Like clip 230, clip 240 has a first side 243 with a tissue contacting surface having a plurality of teeth 246. Second side 245 of clip 240 has a tissue contacting surface with a plurality of teeth 248. Clip 240 is shown in the fully closed position (condition) in FIG. 29A, the fully open position in FIG. 29B, the mostly (semi) open position in FIG. 30, the half-closed position in FIG. 31 and the ¾ closed condition in FIG. 32. The two sides 243, 245 pivot about (around) hinged areas 244a 244b. The first side 243 has an opening 251a and the second side has an opening 251b, preferably centrally located, to receive the clip engagement members for manipulating the clip, i.e., for opening the clip, as described below.

The sheath 250 has an opening or lumen (like channel 218 of sheath 214) to receive a flexible endoscope, colonoscope, laparoscope, etc. as the hollow sheath 250 is configured and dimensioned to be positioned over an endoscope. Extending through the sheath 250 are links 260, 262, having hooks 264, 266, respectively, engageable with openings 251a, 251b in clip 240. The links 260, 262 are each attached to an elongated member which provide actuators (manipulators) for controlling the clip 240. The sheath 250, as well as the other sheaths disclosed herein as alternate embodiments, can be positioned only over a distal region of the endoscope, over a more substantial region of the endoscope or over the entire endoscope. That is, the sheath can be in the form of a hollow sleeve placed over the entire scope or formed as an attachment to the distal end of the scopes or only a portion of the scope.

Figure 34:
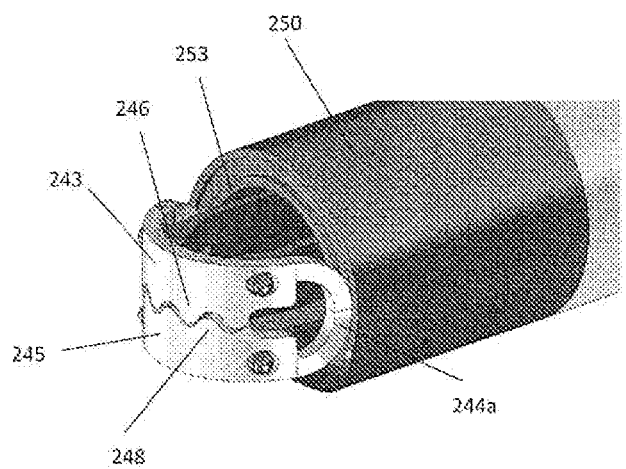
FIG. 34 is a perspective view showing the clip of FIG. 29A mounted to the delivery sheath of the present invention, the clip shown in its normally closed condition.
Figure 35:
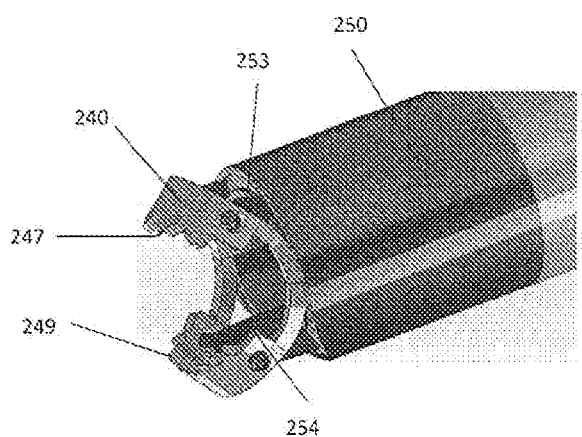
FIG. 35 is a perspective view showing the clip of FIG. 29A mounted to the delivery sheath of the present invention, the clip shown in open condition by a force applied to the clip by pulling the links proximally.
Figure 36:
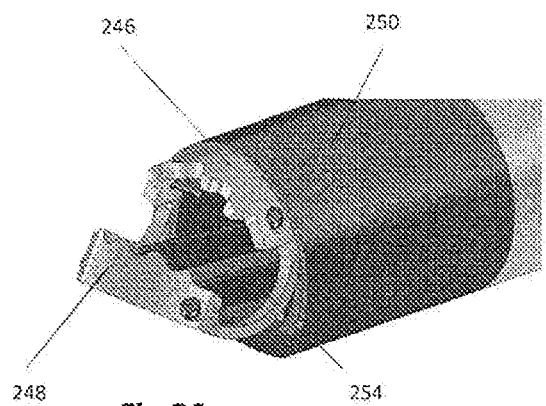
FIG. 36 is a perspective view showing the clip of FIG. 29A mounted to the delivery sheath of the present invention and force applied to only one of the links for asymmetric opening of the clip.
Figure 37:
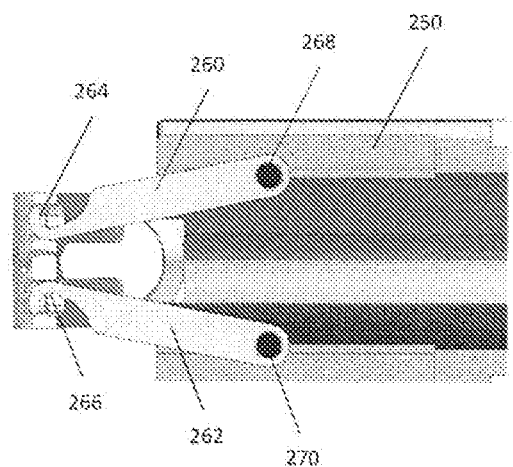
FIG. 37 is a bottom view of an alternate embodiment of the clip deployment system showing two links engaging the surgical clip of FIG. 29A, the clip shown in the closed condition.
Figure 38:
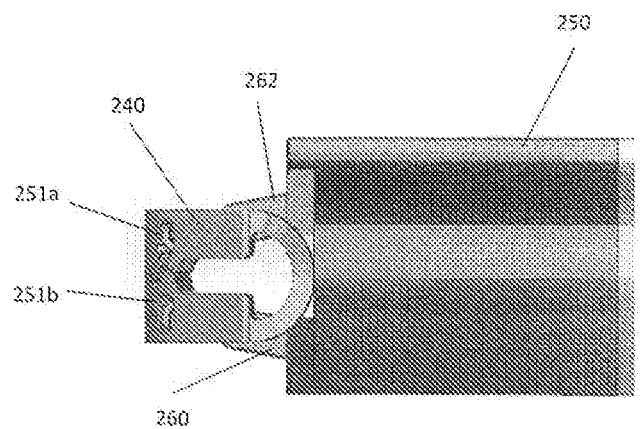
FIG. 38 is a top view of the clip deployment system of FIG. 37.
Figure 39:
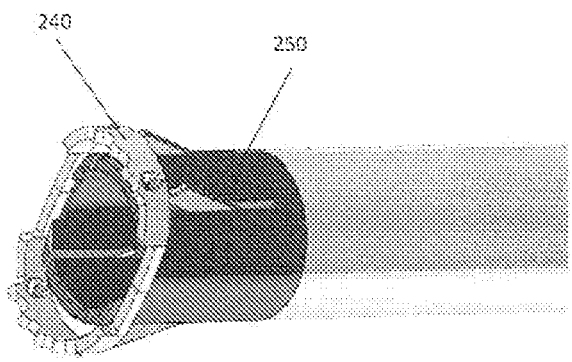
FIG. 39 is a perspective view of the clip deployment system of FIG. 37 showing the clip in the open condition.

For insertion and deployment of clip 240 and with reference to FIGS. 34-39, in the initial position, the elongated members and attached links 260, 262, with their hooks 264, 266 are in the extended position with the preloaded clip in the closed position as shown in FIGS. 34, 37 and 38. In this closed position, the teeth 246, 248 of tissue contacting surfaces 247, 249, respectively, can partially or alternatively fully intermesh. With hooks 264, 266 engaged with the clip 240 (through openings 251a, 251b) as shown in FIGS. 37 and 38, no force is applied to the clip 240 as no force is applied to the links 260, 262 by the elongated members which are attached at pivots 268, 270 at the proximal ends of links 260, 262. To controllably open the clip 240, a pull force is applied to the hooks 264, 266 via the elongated members by pulling the elongated members proximally. This causes the two opposing sides of the clip to be pivoted away from each other about hinges 244a, 244b as the hinged regions 244a, 244b are held stationary as they abut against a distal end of the sheath 250 as shown and a force is applied to the clip sides to open the clip to the position of as shown in FIG. 35. Note as the clip is opened, the tissue contacting surfaces 247, 249 (and their respective teeth 246, 248) are pivoted away from each other to open a space for receipt of tissue. Note in FIG. 35, both links are pulled with equal force resulting in symmetrical opening of the clip. In FIG. 36, a force is applied to only one side of the clip to cause asymmetrical opening of the clip 240 if desired.

After the clip is moved to the open position, the scope can be inserted through the opening, the tissue retractor inserted to retract tissue in the clip opening, etc. in the same manner as discussed above in conjunction with FIGS. 26A-28. Thus the method of applying the clip described with respect to FIGS. 26A-28, and its alternatives described above, are fully applicable to the clip deployment method for clip 240. Thus, for example, like clip 230, clip 240 can be repositioned after placement if desired and can be controllably (e.g., incrementally) opened and closed.

Figure 40:
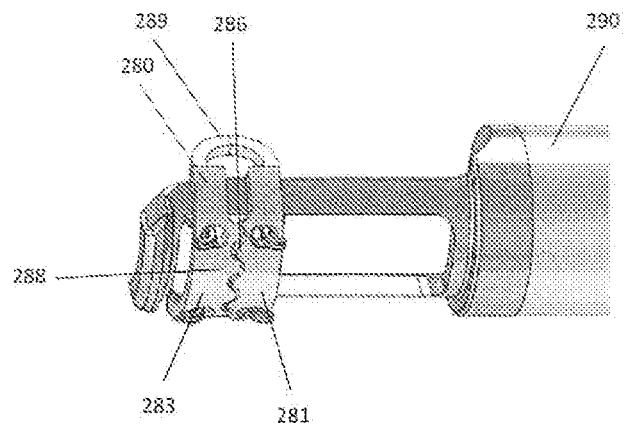
Figure 41:
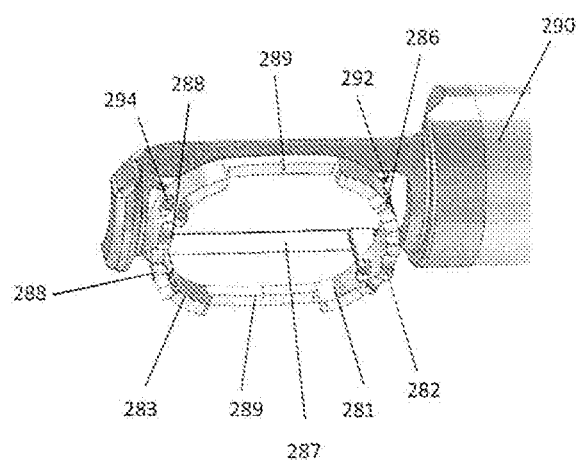

FIGS. 40-41 illustrate a laterally oriented clip in accordance with an alternate embodiment of the present invention. Clip 280 is shown by way of example, it being understood that the other clips disclosed herein (the various radially expandable clips and the various hinged clips) can be mounted laterally in a similar manner. Clip 280 is mounted so that the teeth 286, 288 on tissue contacting surfaces 282, 284 on opposing sides 281, 283 of clip 280 are axially spaced. That is, teeth 286 are proximal of teeth 288 in the pre-loaded closed position of the clip 280. The hinged regions 289 are transverse to a longitudinal axis of the sheath 290.

To move the clip 280 from its closed position of FIG. 40 to its open position of FIG. 41, the proximal link 292 which engages the first (proximal) side 281 of clip 240 is pulled proximally while the distal link 294 which engages the second (distal) side 283 of the clip is held stationary or substantially stationary. Note the links 292, 294 can engage the clip 240 via hooks extending through holes on opposing sides of the clip or by other ways such as the other arrangements/configurations disclosed herein in other clip deployment systems. As the proximal link 292 is pulled proximally, it moves the first side 281 of clip 240 away from the second side 283 to pivot the first side 281 about the hinge 289 to provide an opening 287 for tissue. Note in this open position, the tissue contacting surfaces 282, 284 face laterally, i.e., away from the longitudinal axis rather than along the longitudinal axis as in the distal facing clip of FIG. 39. Tissue is then retracted into the opening 287 and then the link 292 is moved distally toward second side 283, thereby returning (pivoting) the clip 240 back to its closed position. Such lateral orientation can be useful in certain clinical applications where it would be beneficial to approach the defect in the lateral manner disclosed. Note in this lateral orientation embodiment, the clip can remain closed when the scope is retracted.

Note the clips disclosed herein can be utilized in various clinical applications, including for example, over fistulas, diverticula, bleeding GI tract ulcers, hemorrhoids, repair of surgical colorectal anastomotic and gastric leaks, full and partial endoscopic resection, endoscopic bariatric procedures including revisions of failing bariatric gastric bypass surgery, full or partial thickness defects in the GI tract, e.g., colon, on other locations in the body.

Although the apparatus and methods of the subject invention have been described with respect to preferred embodiments, those skilled in the art will readily appreciate that changes and modifications may be made thereto without departing from the spirit and scope of the present invention as defined by the appended claims.

What is claimed is:

1. A system for compressing body tissue comprising:
   a) a surgical clip for delivery by an endoscope, the clip having a first tissue contacting surface and a second tissue contacting surface, the clip movable from a closed position to an open position, in the open position the clip receives tissue between the first and second tissue contacting surfaces and in the closed position the clip compresses tissue between the first and second tissue contacting surfaces; and
   b) a clip deployment device configured to be placed over the endoscope and having a first clip engagement member and a second clip engagement member engageable with the clip, the first and second clip engagement members movable between first and second positions to controllably move the clip from the closed position to the open position and to move the clip from the open position to the closed position to control release of the clip onto tissue.

2. The system of claim 1, wherein the first and second clip engagement members are movable independently.

3. The system of claim 1, wherein the clip is normally in the closed position and the first and second engagement members apply a force to different sides of the clip to open the clip from the closed position.

4. The system of claim 1, wherein the first tissue contacting surface has a first plurality of teeth and the second tissue contacting surface has a second plurality of teeth.

5. The system of claim 1, wherein the clip is movable from a closed position to a radially expanded open position.

6. The system of claim 1, wherein the first tissue contacting surface is on a first side of the clip and the second tissue contacting surface is on a second side of the clip, and the first clip engagement member engages the first side of the clip and the second engagement member engages the second side of the clip.

7. The system of claim 1, wherein the first clip engagement member comprises a first link and the second clip engagement member comprises a second link, and a first actuator is operatively connected to the first link and a second actuator is operatively connected to the second link, wherein slidable movement of the first actuator in an axial direction pivots the first link to effect spreading of the first side of the clip in a first direction away from a center of the clip and slidable movement of the second actuator in an axial direction pivots the second link to effect spreading of the second side of the clip in a second direction away from the center of the clip.

8. The system of claim 1, wherein the first clip engagement member comprises a first link and the second clip engagement member comprises a second link, and a first actuator is operatively connected to the first link and a second actuator is operatively connected to the second link, wherein slidable movement of the first actuator axially moves the first link to effect spreading of the first side of the clip in a first direction away from a center of the clip and slidable movement of the second actuator axially moves the second link to effect spreading of the second side of the clip in a second direction away from the center of the clip.

9. The system of claim 1, further comprising a sheath, the first and second clip engagement members extending through the sheath, the sheath configured for mounting over an endoscope and the clip mounted on the sheath.

10. The system of claim 9, wherein the clip is mounted on the sheath facing distally, wherein movement of one of the first and second clip engagement members changes the orientation of the clip to an angle to a longitudinal axis of the sheath.

11. The system of claim 1, wherein after placement of the clip in the closed position on tissue and the clip is disconnected from the clip deployment device, the clip deployment device is reconnectable to the clip so the clip is movable back to the open position by reverse movement of the first and second clip engagement members.

12. The system of claim 1, wherein the clip has a closed geometric shape with looped ends.

13. A system for compressing body tissue comprising:
   a) a surgical clip, the clip having a first tissue contacting surface and a second tissue contacting surface, the clip movable from a closed position to an expanded open position, in the open position the clip receives tissue between the first and second tissue contacting surfaces and in the closed position the clip compresses tissue between the first and second tissue contacting surfaces; and
   b) a clip deployment device having a sheath and a first clip engagement member having a longitudinal axis and a first end portion and a second clip engagement member having a longitudinal axis and a second end portion, the sheath mountable over at least a distal portion of an endoscope so the endoscope is slidable within the sheath, the first and second clip engagement members engageable with the clip and movable axially with respect to the sheath to effect opening of the clip, wherein a radial distance between the first and second end portions is changeable to enable engagement of the clip in the open position and in the closed position.

14. The system of claim 13, wherein the sheath has a first channel to receive the first clip engagement member and a second channel to receive the second clip engagement member.

15. The system of claim 13, wherein the first clip engagement member comprises a pair of jaws for grasping the clip on a first side and the second clip engagement member comprises a pair of jaws for grasping the clip on a second side.

16. The system of claim 13, wherein the first and second clip engagement members have flexible shafts, the shafts flexing inwardly toward a longitudinal axis of the sheath when the clip is in the closed position and moving away from the longitudinal axis to move the clip to the open position.

17. The system of claim 13, wherein the endoscope is slidable distally from the sheath for visualizing tissue distal of the sheath.

18. The system of claim 17, wherein the sheath is slidable proximally relative to the clip after positioning of the clip on tissue in the closed position without effecting movement of the clip from the closed position to increase the field of vision of the endoscope.

19. The system of claim 13, wherein the clip is radially expandable so that movement of the first and second clip engagement members spreads first and second sides of the clip away from each other to open the clip.

20. The system of claim 13, wherein the clip is biased to the closed position and the first and second clip engagement members apply a force to first and second sides of the clip to force the clip to the open position, wherein release of the force returns the clip to its normally closed position.

\* \* \* \* \*